US012806183B2

(12) United States Patent
Burke et al.

(10) Patent No.: US 12,806,183 B2
(45) **Date of Patent: *Nov. 24, 2026**

(54) FORMULATIONS OF A SOMATOSTATIN MODULATOR

(71) Applicant: Crinetics Pharmaceuticals, Inc., San Digeo, CA (US)

(72) Inventors: Gerald Burke, San Diego, CA (US); Ian Yates, Bend, OR (US); Hannah Bulovsky, Bend, OR (US); Kyle Kyburz, Bend, OR (US); Clayton Tyler, Bend, OR (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 278 days.

This patent is subject to a terminal disclaimer.

(21) Appl. No.: 18/599,998

(22) Filed: Mar. 8, 2024

(65) Prior Publication Data

US 2024/0398782 A1 Dec. 5, 2024

Related U.S. Application Data

(63) Continuation of application No. 17/584,225, filed on Jan. 25, 2022, now Pat. No. 11,957,674, which is a continuation of application No. 17/468,440, filed on Sep. 7, 2021, now Pat. No. 11,266,641.

(60) Provisional application No. 63/076,024, filed on Sep. 9, 2020.

(51) Int. Cl.

| | |
|---|---|
| ***A61K 31/47*** | (2006.01) |
| ***A61K 9/00*** | (2006.01) |
| ***A61K 9/20*** | (2006.01) |
| ***A61K 31/4709*** | (2006.01) |
| ***A61K 45/06*** | (2006.01) |
| ***A61P 35/00*** | (2006.01) |

(52) U.S. Cl.

CPC ........ *A61K 31/4709* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 45/06* (2013.01)

(58) Field of Classification Search

CPC ................................ A61K 31/47; A61P 35/00

USPC ........................................................ 514/314

See application file for complete search history.

(56) References Cited

U.S. PATENT DOCUMENTS

| | | | |
|---|---|---|---|
| 7,115,634 | B2 | 10/2006 | Thurieau et al. |
| 7,648,984 | B2 | 1/2010 | Miller et al. |
| 7,767,817 | B2 | 8/2010 | Wang et al. |
| 9,120,749 | B2 | 9/2015 | Matsuo et al. |
| 9,309,222 | B2 | 4/2016 | Leonard et al. |
| 9,643,951 | B2 | 5/2017 | Ishida et al. |
| 9,896,432 | B2 | 2/2018 | Zhao et al. |
| 9,902,703 | B2 | 2/2018 | Zhao et al. |
| 9,957,267 | B2 | 5/2018 | Zhu et al. |
| 10,351,547 | B2 | 7/2019 | Zhao et al. |
| 10,464,918 | B2 | 11/2019 | Reddy et al. |
| 10,597,377 | B2 | 3/2020 | Zhao et al. |
| 10,696,689 | B2 | 6/2020 | Han et al. |
| 10,875,839 | B2 | 12/2020 | Zhao et al. |
| 10,889,561 | B2 | 1/2021 | Reddy et al. |
| 11,072,598 | B2 | 7/2021 | Han et al. |
| 11,266,641 | B1 | 3/2022 | Burke et al. |
| 11,414,397 | B2 | 8/2022 | Zhao et al. |
| 11,957,574 | B2 | 4/2024 | Levi |
| 11,957,674 | B2 | 4/2024 | Burke et al. |
| 12,617,767 | B2 | 5/2026 | Reddy et al. |
| 2003/0153553 | A1 | 8/2003 | Mattei et al. |
| 2005/0009815 | A1 | 1/2005 | Devita et al. |
| 2007/0225366 | A1 | 9/2007 | Xiang et al. |
| 2009/0258853 | A1 | 10/2009 | Eastman et al. |
| 2010/0256184 | A1 | 10/2010 | Rowe et al. |
| 2012/0329741 | A1 | 12/2012 | Oyelere et al. |
| 2014/0038990 | A1 | 2/2014 | Buschmann et al. |
| 2014/0228417 | A1 | 8/2014 | Mizhiritskii et al. |
| 2014/0315924 | A1 | 10/2014 | Schwab et al. |
| 2015/0232478 | A1 | 8/2015 | Ishida et al. |
| 2015/0239900 | A1 | 8/2015 | Li et al. |
| 2015/0284337 | A1 | 10/2015 | Aubele et al. |
| 2017/0049850 | A1 | 2/2017 | Kuzma et al. |
| 2017/0096422 | A1 | 4/2017 | Tsukamoto et al. |
| 2018/0016252 | A1 | 1/2018 | Zhao et al. |
| 2019/0211008 | A1 | 7/2019 | Gallina et al. |
| 2019/0382367 | A1 | 12/2019 | Zhao et al. |
| 2020/0048219 | A1 | 2/2020 | Reddy et al. |
| 2020/0190053 | A1 | 6/2020 | Zhao et al. |
| 2020/0237733 | A1 | 7/2020 | Geissler et al. |
| 2021/0087165 | A1 | 3/2021 | Reddy et al. |

(Continued)

FOREIGN PATENT DOCUMENTS

| | | | |
|---|---|---|---|
| CA | 2925651 | A1 | 4/2015 |
| CN | 1627945 | A | 6/2005 |

(Continued)

OTHER PUBLICATIONS

Co-pending U.S. Appl. No. 18/587,187, inventors Reddy; Jayachandra P. et al., filed on Feb. 26, 2024.

(Continued)

*Primary Examiner* — Raymond J Henley, III

(74) *Attorney, Agent, or Firm* — WILSON SONSINI GOODRICH & ROSATI

(57) ABSTRACT

Described herein are formulations of a somatostatin modulator, methods of making such formulations, and methods of using such formulations in the treatment of conditions, diseases, or disorders that would benefit from modulation of somatostatin activity.

21 Claims, 2 Drawing Sheets

(56) References Cited

U.S. PATENT DOCUMENTS

| | | | |
|---|---|---|---|
| 2021/0171492 A1 | 6/2021 | Zhao et al. |
| 2022/0071986 A1 | 3/2022 | Burke et al. |
| 2022/0143007 A1 | 5/2022 | Burke et al. |
| 2022/0267295 A1 | 8/2022 | Reddy et al. |
| 2022/0380337 A1 | 12/2022 | Zhao et al. |
| 2022/0387420 A1 | 12/2022 | Madan et al. |
| 2024/0366587 A1 | 11/2024 | Madan et al. |
| 2024/0376067 A1 | 11/2024 | Reddy et al. |
| 2025/0228842 A1 | 7/2025 | Krasner et al. |
| 2026/0008767 A1 | 1/2026 | Zhao et al. |

FOREIGN PATENT DOCUMENTS

| | | | |
|---|---|---|---|
| CN | 102171202 A | 8/2011 |
| CN | 105593221 A | 5/2016 |
| CN | 108473489 A | 8/2018 |
| CN | 110913840 A | 3/2020 |
| EP | 3053916 A1 | 8/2016 |
| JP | 2009520690 A | 5/2009 |
| KR | 20160062023 A | 6/2016 |
| WO | WO-03045920 A1 | 6/2003 |
| WO | WO-03066055 A1 | 8/2003 |
| WO | WO-2006070284 A1 | 7/2006 |
| WO | WO-2007067495 A2 | 6/2007 |
| WO | WO-2007098214 A1 | 8/2007 |
| WO | WO-2007103554 A1 | 9/2007 |
| WO | WO-2008051272 A2 | 5/2008 |
| WO | WO-2010019239 A2 | 2/2010 |
| WO | WO-2010026121 A1 | 3/2010 |
| WO | WO-2010041054 A1 | 4/2010 |
| WO | WO-2011019413 A1 | 2/2011 |
| WO | WO-2012027731 A2 | 3/2012 |
| WO | WO-2012151567 A1 | 11/2012 |
| WO | WO-2012162254 A1 | 11/2012 |
| WO | WO-2012163354 A1 | 12/2012 |
| WO | WO-2013020993 A1 | 2/2013 |
| WO | WO-2013050996 A2 | 4/2013 |
| WO | WO-2014042945 A1 | 3/2014 |
| WO | WO-2014043208 A1 | 3/2014 |
| WO | WO-2014114575 A1 | 7/2014 |
| WO | WO-2015024010 A2 | 2/2015 |
| WO | WO-2015046482 A1 | 4/2015 |
| WO | WO-2015146929 A1 | 10/2015 |
| WO | WO-2016049568 A1 | 3/2016 |
| WO | WO-2016094662 A1 | 6/2016 |
| WO | WO-2016126830 A1 | 8/2016 |
| WO | WO-2017003724 A1 | 1/2017 |
| WO | WO-2017075340 A1 | 5/2017 |
| WO | WO-2017083431 A2 | 5/2017 |
| WO | WO-2017106607 A1 | 6/2017 |
| WO | WO-2018013676 A1 | 1/2018 |
| WO | WO-2018208987 A2 | 11/2018 |
| WO | WO-2019030302 A1 | 2/2019 |
| WO | WO-2019143718 A1 | 7/2019 |
| WO | WO-2020061046 A1 | 3/2020 |
| WO | WO-2021011641 A1 | 1/2021 |
| WO | WO-2022055880 A1 | 3/2022 |
| WO | WO-2022251212 A2 | 12/2022 |
| WO | WO-2023137018 A1 | 7/2023 |

OTHER PUBLICATIONS

Co-pending U.S. Appl. No. 18/762,266, inventors Madan; Ajay et al., filed on Jul. 2, 2024.

Antunes et al. New and emerging pharmacological treatment options for acromegaly. Expert Opin Pharmacother. 22(12):1615-1623 (2021).

Bastin et al. Salt Selection and Optimisation Procedures for Pharmaceutical New Chemical Entities. Org. Proc. Res. Dev. 4(5):427-435 (2000).

Berge et al., Pharmaceutical Salts. Journal of Pharmaceutical Sciences 66(1):1-19 (1977).

Betz et al. Suppression of Growth Hormone and Insulin-Like Growth Factor 1 in Rats After Oral Administration of CRN00808, a Small Molecule, sst2 Selective Somatostatin Biased Agonist. Poster SUN-604 #6743 (2018).

Brazeau et al. Hypothalamic polypeptide that inhibits the secretion of immunoreactive pituitary growth hormone. Science 179:77-79 (1973).

Bundgaard. Design and Application of Pro-drugs. A Textbook of Drug Design and Development. pp. 113-191 (1991).

Carmichael et al. Acromegaly clinical trial methodology impact on reported biochemical efficacy rates of somatostatin receptor ligand treatments: A Meta-Analysis. J Clin Endocrinol Metab 99:1825-1833 (2014).

Carroll et al. Acromegaly. In: Feingold KR, Anawalt B, Boyce A, et al., editors. Endotext [Internet]. South Dartmouth (MA): MDText.com, Inc.; 2000—. Available from: https://www.ncbi.nlm.nih.gov/books/NBK279097/ [Updated Sep. 7, 2022].

Cescato et al. Agonist-Biased Signaling at the sst2A Receptor: The Multi-Somatostatin Analogs KE108 and SOM230 Activate and Antagonize Distinct Signaling Pathways. Mol Endocrinol 24(1):240-249 (2010).

Chiang et al. In vitro and in vivo evaluation of amorphous solid dispersions generated by different bench-scale processes, using griseofulvin as a model compound. AAPS J 15(20:608-617 (2013).

Crinetics Pharmaceuticals. Acromegaly KOL Event. Presentation. Nov. 20, 2020.

Diabetes-Test information on the website of the CDC (2023).

Esch et al. Primary structure of ovine hypothalamic somatostatin-28 and somatostatin-25. PNAS USA 77:6827-6831 (1980).

Florence. Polymorph screening in pharmaceutical development. European Pharmaceutical Review. Available at https://www.europeanpharmaceuticalreview.com/article/3659/polymorph-screening-in-pharmaceutical-development/ [retrieved on Mar. 7, 2018] (2010).

Gadelha et al. Acrobat Edge Phase 2 Study: Safety and Efficacy of Switching Injected Long-Acting Somatostatin Receptor Ligands (SRLs) to Once Daily Oral Paltusotine. Poster #7452 (2021).

Gadelha et al. Safety and efficacy of switching injected peptide long-acting somatostatin receptor ligands to once daily oral paltusotine: Acrobat edge phase 2 study. Journal of the Endocrine Society 5.Supplement_1 (2021):A526-A527 (2021).

Gadelha et al. Safety and Efficacy of Switching Injected Peptide Long-Acting Somatostatin Receptor Ligands to Once Daily Oral Paltusotine: Acrobat Edge Phase 2 Study. Poster Presented at ENDO 2021 (Mar. 20-23, 2021).

Gadelha et al. The Future of Somatostatin Receptor Ligands in Acromegaly. J Clin Endocrinol Metab. 107(2):297-308 (2022).

Gradiz et al. MIA PaCa-2 and PANC-1—pancreas ductal adenocarcinoma cell lines with neuroendocrine differentiation and somatostatin receptors. Scientific Reports 6:21648 (15 pgs.) (2016).

Henry et al., Hyperglycemia associated with pasireotide: results from a mechanistic study in healthy volunteers. J Clin. Endocrinol. Metab. 98(8):3446-3453 (2013).

Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).

Katznelson et al. Acromegaly: an endocrine society clinical practice guideline. J Clin Endocrinol Metab 99(11):3933-3951 (2014).

Kuhn et al. Pharmacokinetic study and effects on growth hormone secretion in healthy volunteers of the new somatostatin analogue BIM 23014. Eur J Clin Pharmacol 45:73-77 (1993).

Luo et al. Pharmacokinetics and Safety of an Improved Oral Formulation of Paltusotine, a Selective, Non-Peptide Somatostatin Receptor 2 (SST2) Agonist for the Treatment of Acromegaly. Poster Presented at ENDO 2021 (Mar. 20-23, 2021).

Madan et al. Paltusotine, a novel oral once-daily nonpeptide SST2 receptor agonist, suppresses GH and IGF-1 in healthy volunteers. Pituitary 25(2):328-339 (2022).

Madan et al. Absolute Oral Bioavailability and Absorption, Metabolism, Excretion of [14C]—Labeled Paltusotine (CRN00808), An Orally Bioavailable, Nonpeptide, Selective, Somatostatin Receptor 2 (SST2) Biased Agonist for the Treatment of Acromegaly. Poster Presented at the virtual European Congress of Endocrinology (eECE) on Sep. 5-9, 2020.

Madan et al. Final Results from the First in Man Phase 1 Clinical Trial of CRN00808, an Orally Bioavailable sst2-Selective, Nonpeptide

(56) References Cited

OTHER PUBLICATIONS

Somatostatin Biased Agonist, for the Treatment of Acromegaly: Safety, Pharmacokinetics, Pharmacodynamics, and Midazolam Drug Interaction in Healthy Volunteers. Poster Presented at ENDO 2019 (Mar. 23-26, 2019).
Madan et al. OR23-05 Human Absorption, Metabolism, Excretion, and Absolute Oral Bioavailability of 14C-CRN00808, an Orally Bioavailable, Nonpeptide, Selective, Somatostatin Receptor 2 (sST2) Biased Agonist for the Treatment of Acromegaly. J Endocr Soc. 4(Suppl 1):A352-A353. Published online May 8, 2020.
Maia et al. Novel therapies for acromegaly. Endocrine Connections 9(12):R274-R285 (2020).
Mazziotti et al. Effects of high-dose octreotide LAR on glucose metabolism in patients with acromegaly inadequately controlled by conventional somatostatin analog therapy. Eu J Endocrinol 164:341-347 (2011).
Mazziotti et al., Effects of somatostatin analogs on glucose homeostasis: a metaanalysis of acromegaly studies. J Clin. Endocrinol. Metab. 94(5):1500-1508 (2009).
NCT03792555 ClinicalTrials.gov (Jan. 3, 2019).
Paltusotine (CRN00808), Evidence from the website of the MedChemExpress (2023).
Parkinson et al., A comparison of the effects of pegvisomant and octreotide on glucose, insulin, gastrin, cholecystokinin, and pancreatic polypeptide responses to oral glucose and a standard mixed meal. J. Clin. Endocrinol. Metab. 87:1797-1804 (2002).
Patel et al. Somatostatin receptors. Trends Endocrinol Metab 8:398-405 (1997).
Paudel et al. Manufacturing of solid dispersions of poorly water soluble drugs by spray drying: Formulation and process considerations. International Journal of Pharmaceutics. 453(1):253-284 (2013).
PCT/US2017/041694 International Search Report and Written Opinion dated Dec. 12, 2017.
PCT/US2019/013844 International Search Report and Written Opinion dated May 1, 2019.
PCT/US2020/042119 International Search Report and Written Opinion dated Nov. 5, 2020.
PCT/US2021/049282 International Search Report and Written Opinion dated Dec. 22, 2021.
PCT/US2022/030721 International Search Report and Written Opinion dated Oct. 17, 2022.
PCT/US2022/030721 Invitation to Pay Additional Fees dated Jul. 26, 2022.
Pradayrol et al. N-terminally extended somatostatin: the primary structure of somatostatin-28. FEBS Letters 109:55-58 (1980).
Prasoon et al. Role of somatostatin and somatostatin receptor type 2 in postincisional nociception in rats. Neropeptides 49:47-54 (2015).
Pubchem-SID: 374408995 Deposit Date: Jun. 23, 2018 (Jun. 23, 2018).
Quabbe et al., Dose-response study and long term effect of the somatostatin analog octreotide in patients with therapy-resistant acromegaly. J. Clin. Endocrinol. Metab. 68:873-881 (1989).
Randeva et al. Acrobat Advance: long-term safety and efficacy results of paltusotine for the treatment of acromegaly. Poster P80 (2021).
Reisine et al. Molecular biology of somatostatin receptors. Endocr Rev 16:427-442 (1995).
Rico, Elizabeth et al., Selective Somatostatin 5 (SST5) and Somatostatin 2 (SST2) Nonpeptide Agonists Potently Suppress Glucose- and Tolbutamide-Stimulated Dynamic Insulin Secretion From Isolated Human Islets . J Endocrine Soc 5(Supp I):A325 (Apr.-May 2021).
Sandret et al. Place of cabergoline in acromegaly: a meta-analysis. J Clin Endocrinol Metab 96(5):1327-1335 (2011).
Song et al. Amine-Mediated Transimination and Aromatization-Triggered Domino Reaction in the Synthesis of Polyfunctionalized 4-Aminoquinolines. Org Lett 18(20):5328-5331 (2016).
Stahl et al.: Handbook of Pharmaceutical Salts. Verlag Helvetica Chimica Acta, Zurich (2002).
Stumvoll et al. Use of the oral glucose tolerance test to assess insulin release and insulin sensitivity. Diabetes Care 23(3):295-301 (2000).
Take on an Empty Stomach. How Do You Know When Your Stomach Is Empty? WRAL.News (Oct. 1, 2018).
Tiberg et al. Octreotide s.c. depot provides sustained octreotide bioavailability and similar IGF-1 suppression to octreotide LAR in healthy volunteers. Br J Clin Pharmacol 80:460-472 (2015).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).
Young et al. SUN-125 Phase lb Study of Dual Therapy with an Aromatase Inhibitor Exemestane and Carboplatin-Based Therapy for Postmenopausal Women with Advanced Non-Small Cell Lung Cancer, Journal of the Endocrine Society. Tumor Biology: Diagnostics, Therapies, Endocrine Neoplasias, and Hormone Dependent Tumors. Available at https://doi.org/10.1210/jendso/bvaa046.695 Journal of the Endocrine Society 4(Supp 1):A352 (Abstract).
Zhao et al. Discovery of nonpeptide 3,4-dihydroquinazoline-4-carboxamides as potent and selective sst2 agonists. Bioorg Med Chem Lett 30(17):127391 (2020).
Hirayama Yoshinaki. The Organic Compound Crystal Production Handbook. (pp. 17, 23, 37, 40, 45, 51, 57, 65) (2008).
Pharmaceutical Affairs and Pharmaceutical Safety Bureau Examination and Management Department Chief Administrative Agency (pp. 1-11) (1998).
Wermuth, C. G. Knitting, Winding under the latest medicinal chemicals. Technomere (pp. 347-365) (1999).
Liu, Yihuan et al. Study on the Dissolution Model of Efavirenz in Solid Dispersion Based on HPMCAS Carrier. Chinese Journal of Modern Applied Pharmacy 9:1096-1101 (2020) (English Abstract).
Adams, Jared R. et al. Living With Neuroendocrine Tumors: Assessment of Quality of Life Through a Mobile Application. JCO Clinical Cancer Informatics 3:1-10 (2019).
Boyd, April E. et al. Improving the Success Rate of Gluteal Intramuscular Injections. Pancreas 42(5):878-882 (2013).
Caplin, Me et al. Lanreotide in metastatic enteropancreatic neuroendocrine tumors. The New England Journal of Medicine 371(16):1556-1557 (2014).
Chan, David L. et al. Developments in the treatment of carcinoid syndrome—impact of telotristat. Ther Clin Risk Manag 14:323-329 (2018).
Chan, Ja et al. Medical Management of Pancreatic Neuroendocrine Tumors: Current and Future Therapy. Surg Oncol Clin N Am 25(2):423-437 (2016).
ClinicalTrials.gov Identifier: NCT03789656. An Study to Evaluate the Safety and Efficacy of Paltusotine for the Treatment of Acromegaly (Acrobat Edge). Record created Dec. 27, 2018. pp. 1-8. [retrieved on Aug. 2, 2024] Available at URL: https://clinicaltrials.gov/study/NCT03789656.
Co-pending U.S. Appl. No. 18/727,827, inventors Krasner; Alan S. et al., filed on Jul. 10, 2024.
Crinetics Therapeutics 2021 Clinical Strategy and 2020 Financial Results Mar. 30, 2021. Crinetics Pharmaceuticals, Inc. (pp. 1-12) (2021).
Crinetics Therapeutics Corporate Presentation Jan. 2021. Crinetics Pharmaceuticals, Inc. (1-38) (2021).
Crinetics Therapeutics Corporate Presentation Mar. 2021. Crinetics Pharmaceuticals, Inc. (pp. 1-43) (2021).
Crinetics Therapeutics Corporate Presentation Sep. 2020. Crinetics Pharmaceuticals, Inc. (pp. 1-34) (2020).
Halperin, DM et al. Frequency of carcinoid syndrome at neuroendocrine tumour diagnosis: a population-based study. Lancet Oncol 18(4):525-534 (2017).
Kunz PL. Carcinoid and neuroendocrine tumors: building on success. J Clin Oncol. 33(16):1855-1863 (2015).
Kvols, LK et al. Treatment of the malignant carcinoid syndrome. Evaluation of a long-acting somatostatin analogue. N Engl J Med 315(11):663-666 (1986).
Lagast, Hjalmar et al. Dose selection for paltusotine, a once daily oral nonpeptide, somatostatin receptor 2 ligand, for the treatment of patients with carcinoid syndrome (CS). Poster presented at North American Neuroendocrine Tumor Society NET Medical Symposium Nov. 4-6, 2021 (1 pg.).

(56) References Cited

OTHER PUBLICATIONS

Naraev, Boris G. et al. Management of Diarrhea in Patients With Carcinoid Syndrome. Pancreas 48(8):961-972 (2019).
Oronsky, B. et al. Nothing But NET: A Review of Neuroendocrine Tumors and Carcinomas. Neoplasia 19(12):991-1002 (2017).
PCT/US2023/010493 International Search Report and Written Opinion dated Apr. 25, 2023.
Rindi, Guido, and Frediano Inzani. Neuroendocrine Neoplasm Update: Toward Universal Nomenclature. Endocrine-Related Cancer 27(6):R211-R218 (2020).
Rinke, A et al. Placebo-controlled, double-blind, prospective, randomized study on the effect of octreotide LAR in the control of tumor growth in patients with metastatic neuroendocrine midgut tumors: a report from the PROMID Study Group. J Clin Oncol 27(28):4656-4663 (2009).
Sandostatin LAR Prescribing Information. U.S. Food & Drug Administration, Mar. 30, 2021; [retrieved on Aug. 2, 2024]. Available at URL:https://www.accessdata.fda.gov/drugsatfda_docs/label/2021/021008s041lbl.pdf pp. 1-19.
Shaunfield, Sara et al. Development of the Functional Assessment of Cancer Therapy—Carcinoid Syndrome Symptom Index. Neuroendocrinology 111(9):850-862 (2021).
Somatuline Prescribing Information. U.S. Food & Drug Administration, Dec. 12, 2018; [retrieved on Aug. 2, 2024]. Available at URL:https://www.accessdata.fda.gov/drugsatfda_docs/label/2018/022074s022lbl.pdf pp. 1-28.
Strosberg, Jonathan R. et al. Clinical Benefits of Above-standard Dose of Octreotide LAR in Patients With Neuroendocrine Tumors for Control of Carcinoid Syndrome Symptoms: A Multicenter Retrospective Chart Review Study. The Oncologist 19(9):930-936 (2014).
Vinik, Aaron et al. Carcinoid Tumors. Endotext [Internet]. Copyright @ MDText.com, Inc; 2000-2021 (2018).
Co-pending U.S. Appl. No. 19/639,569, inventors Reddy; Jayachandra P. et al., filed on Apr. 6, 2026.
Crinetics Pharmaceuticals, Topline Results from the Acrobat Phase 2 Program in Acromegaly, presentation, (2020). Available at URL:https://crinetics.com/wp-content/uploads/2020/10/ACROBAT-Final-Data-Presentation-102020.pdf pp. 1-27.
Huang, Y. et al. Fundamental aspects of solid dispersion technology for poorly soluble drugs. Acta Pharmaceutica Sinica B, 4(1):18-25 (2014).
Luo, Rosa et al. Pharmacokinetics and safety of an improved oral formulation of paltusotine, a selective, non-peptide somatostatin receptor 2 (SST2) agonist for the treatment of acromegaly. Journal of the Endocrine Society 5(Supplement_1):A524-A525 (2021).

Note: subjects were fasted overnight and 4 hour pose-dose.
20 mg: N=5; 5, 30, 40, and 60 mg: N=6; 10 mg: N=12.
Source data: CRN00808-01

Note: subjects were fasted overnight and 2 hour pose-dose.
20 mg and 60 mg: N=11. Source data: CRN00808-07

Pg=Pentagastrin.
Source data:411291-2017033001-DPK (2017-PK-074)

Pg=Pentagastrin.
Source Data: 409743-2019011101-DPK (2019-PK-026)

FORMULATIONS OF A SOMATOSTATIN MODULATOR

CROSS-REFERENCE TO RELATED APPLICATIONS

This application is a continuation of U.S. patent application Ser. No. 17/584,225, filed Jan. 25, 2022, now U.S. Pat. No. 11,957,674, issued Apr. 16, 2024, which is a continuation of U.S. patent application Ser. No. 17/468,440, filed Sep. 7, 2021, now U.S. Pat. No. 11,266,641, issued Mar. 8, 2022, which claims benefit of U.S. Provisional Patent Application No. 63/076,024, filed on Sep. 9, 2020, each of which is incorporated herein by reference in its entirety.

FIELD OF THE INVENTION

Described herein are pharmaceutical compositions and medicaments comprising a somatostatin modulator, methods of making such pharmaceutical compositions and medicaments and methods of using such pharmaceutical compositions and medicaments in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

In one aspect, provided herein is a spray-dried solid dispersion comprising: (a) 3-[4-(4-amino-piperidin-1-yl)-3-(3,5-difluoro-phenyl)-quinolin-6-yl]-2-hydroxy-benzonitrile, or a pharmaceutically acceptable salt or solvate thereof; and (b) a pharmaceutically acceptable polymer; wherein 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, is dispersed in a polymer matrix formed from the pharmaceutically acceptable polymer. In some embodiments, the pharmaceutically acceptable polymer has a high glass transition temperature (Tg). In some embodiments, the pharmaceutically acceptable polymer comprises polymers of: cellulose optionally functionalized with any combination of alkyl ethers, alkyl esters, phthalate esters; vinyl alcohol; vinyl acetate; propylene glycol; pyrrolidone; vinylpyrrolidone, oxyethylene; oxypropylene; methacrylic acid; methyl methacrylate; ethylene glycol; ethylene glycol glycerides; ethylene oxide; propylene oxide; 2-ethyl-2-oxazoline; maleic acid; methyl vinyl ether; vinyl caprolactam; or combinations thereof.

In some embodiments, the pharmaceutically acceptable polymer is hydroxypropyl methylcellulose (HPMC), hydroxypropyl methyl cellulose acetate succinate (HPMCAS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyvinylpyrrolidone polyvinyl acetate copolymers (PVP/VA), polyethylene polyvinyl alcohol copolymers, polyoxyethylene-polyoxypropylene block copolymers, cellulose acetate phthalate (CAP), hydroxypropyl methyl-cellulose phthalate (HPMCP), co-polymerc of methacrylic acid and methyl methacrylate, polyethylene glycol glycerides composed of mono-, di- and triglycerides and mono- and diesters of polyethylene glycol, hydroxypropylcellulose, copolymers of ethylene oxide and propylene oxide blocks, poly(2-ethyl-2-oxazoline), poly(maleic acid/methyl vinyl ether), polyvinyl caprolactam-polyvinyl acetate-polyethylene glycol graft copolymer, ethylene oxide/propylene oxide tetra functional block copolymer, d-alpha tocopheryl polyethylene glycol 1000 succinate, or combinations thereof. In some embodiments, the pharmaceutically acceptable polymer is hydroxypropyl methyl cellulose acetate succinate (HPMCAS), or polyvinylpyrrolidone polyvinyl acetate copolymers (PVP/VA). In some embodiments, the pharmaceutically acceptable polymer is hydroxypropyl methyl cellulose acetate succinate grade M (HPMCAS-M). In some embodiments, the pharmaceutically acceptable polymer is polyvinylpyrrolidone polyvinyl acetate copolymers in a 6:4 ratio (PVP/VA 64).

In some embodiments, the weight ratio of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, to the pharmaceutically acceptable polymer is from about 1:10 to about 10:1. In some embodiments, the weight ratio of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, to the pharmaceutically acceptable polymer is from about 1:1 to about 1:10. In some embodiments, the weight ratio of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, to the pharmaceutically acceptable polymer is from about 1:4 to about 1:6. In some embodiments, the weight ratio of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, to the pharmaceutically acceptable polymer is from about 1:1.5 to about 1:6.

In some embodiments, the spray-dried solid dispersion comprises at least about 5% by weight of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof. In some embodiments, the spray-dried solid dispersion comprises at least about 10% by weight of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof. In some embodiments, the spray-dried solid dispersion comprises about 15% by weight of 3-[4-(4-amino-piperidin-1-yl)-3-(3,5-difluoro-phenyl)-quinolin-6-yl]-2-hydroxy-benzonitrile, or a pharmaceutically acceptable salt or solvate thereof.

In some embodiments, the spray-dried solid dispersion further comprises a non-aqueous solvent. In some embodiments, the non-aqueous solvent is selected from the group consisting of tert-butanol, n-propanol, n-butanol, isopropanol, ethanol, methanol, acetone, ethyl acetate, acetonitrile, methyl ethyl ketone, methyl isobutyl ketone, methyl acetate, and mixtures thereof. In some embodiments, the non-aqueous solvent is selected from the group consisting of methanol, acetone, and mixtures thereof. In some embodiments, the non-aqueous solvent is methanol.

In some embodiments, 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, is substantially amorphous.

In some embodiments, 3-[4-(4-amino-piperidin-1-yl)-3-(3,5-difluoro-phenyl)-quinolin-6-yl]-2-hydroxy-benzonitrile, or a pharmaceutically acceptable salt or solvate thereof, is 3-[4-(4-amino-piperidin-1-yl)-3-(3,5-difluoro-phenyl)-quinolin-6-yl]-2-hydroxy-benzonitrile monohydrochloride, or solvate thereof.

In another aspect, provided herein is a tablet comprising: the spray-dried solid dispersion described herein; one or more pharmaceutical acceptable ingredients selected from the group consisting of one or more diluents, one or more disintegrants, one or more lubricants, one or more glidants; and optionally one or more film coating agents.

In another aspect, provided herein is a tablet comprising: 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer; one or more pharmaceutical acceptable ingredients selected from the group consisting of one or more diluents, one or more disintegrants, one or more lubricants, one or more glidants; and optionally one or more film coating agents. In some embodiments, 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer is a spray-dried solid dispersion described herein. In some embodiments, the one or more pharmaceutical acceptable ingredients comprise microcrystalline cellulose, mannitol, crospovidone, colloidal silicon dioxide, and magnesium stearate. In some embodiments, the one or more pharmaceutical acceptable ingredients comprise microcrystalline cellulose, mannitol, pregelatinized starch croscarmellose sodium crospovidone, sodium chloride, 1:1 sodium chloride:potassium chloride, colloidal silicon dioxide, and magnesium stearate.

In some embodiments, the tablet comprises about 2% by weight to about 20% by weight of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 2% by weight to about 15% by weight of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, or about 15% by weight of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 10% by weight to about 30% by weight of the polymer matrix formed from the pharmaceutically acceptable polymer. In some embodiments, the tablet comprises about 20% by weight to about 35% by weight of the polymer matrix formed from the pharmaceutically acceptable polymer.

In some embodiments, the tablet comprises about 2% by weight to about 10% by weight of 3-[4-(4-amino-piperidin-1-yl)-3-(3,5-difluoro-phenyl)-quinolin-6-yl]-2-hydroxy-benzonitrile monohydrochloride, or solvate thereof, dispersed in about 10% by weight to about 30% by weight of a polymer matrix formed from a pharmaceutically acceptable polymer; about 40% by weight to about 80% by weight of one or more pharmaceutical acceptable ingredients selected from the group consisting of one or more diluents, one or more disintegrants, one or more lubricants, one or more glidants; and optionally less than about 5% by weight of one or more film coating agents.

In some embodiments, the tablet comprises: about 2% by weight to about 10% by weight of 3-[4-(4-amino-piperidin-1-yl)-3-(3,5-difluoro-phenyl)-quinolin-6-yl]-2-hydroxy-benzonitrile monohydrochloride, or solvate thereof, dispersed in about 10% by weight to about 35% by weight of a polymer matrix formed from a pharmaceutically acceptable polymer; about 40% by weight to about 80% by weight of one or more pharmaceutical acceptable ingredients selected from the group consisting of one or more diluents, one or more disintegrants, one or more lubricants, one or more glidants; and optionally less than about 5% by weight of one or more film coating agents.

In some embodiments, the tablet comprises: about 20% by weight to about 40% of a spray dried dispersion of 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer; about 60% by weight to about 80% by weight of one or more pharmaceutical acceptable ingredients selected from the group consisting of one or more diluents, one or more disintegrants, one or more disintegrant aids, one or more lubricants, one or more glidants; and optionally less than about 5% by weight of one or more film coating agents.

In some embodiments, the spray dried dispersion comprises an about 15/85 to about 35/65 ratio of 3-[4-(4-amino-piperidin-1-yl)-3-(3,5-difluoro-phenyl)-quinolin-6-yl]-2-hydroxy-benzonitrile monohydrochloride, or solvate thereof to a polymer matrix of hydroxypropyl methyl cellulose acetate succinate (HPMCAS), or polyvinylpyrrolidone polyvinyl acetate copolymers (PVP/VA).

In some embodiments, the tablet comprises: about 20% by weight to about 35% of a spray dried dispersion of 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer; wherein the spray dried dispersion comprises an about 15/85 to about 35/65 ratio of 3-[4-(4-amino-piperidin-1-yl)-3-(3,5-difluoro-phenyl)-quinolin-6-yl]-2-hydroxy-benzonitrile monohydrochloride, or solvate thereof to a polymer matrix of hydroxypropyl methyl cellulose acetate succinate (HPMCAS), or polyvinylpyrrolidone polyvinyl acetate copolymers (PVP/VA); about 60% by weight to about 80% by weight of one or more pharmaceutical acceptable ingredients selected from the group consisting of microcrystalline cellulose, mannitol, pregelatinized starch, croscarmellose sodium, crospovidone, sodium chloride, 1:1 sodium chloride:potassium chloride, silicon dioxide, and magnesium stearate; optionally less than about 5% by weight of one or more film coating agents.

In some embodiments, the tablet comprises: about 20%, about 21%, about 22%, about 23%, about 24%, about 25%, about 26%, about 27%, about 28%, about 29%, about 30%, about 31%, about 32%, about 33%, about 34%, or about 35% by weight of a spray dried dispersion of 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer; wherein the spray dried dispersion comprises an about 15/85 or about 35/65 ratio of 3-[4-(4-amino-piperidin-1-yl)-3-(3,5-difluoro-phenyl)-quinolin-6-yl]-2-hydroxy-benzonitrile monohydrochloride, or solvate thereof to a polymer matrix of hydroxypropyl methyl cellulose acetate succinate (HPMCAS), or polyvinylpyrrolidone polyvinyl acetate copolymers (PVP/VA); about 60% by weight to about 80% by weight of one or more pharmaceutical acceptable ingredients selected from the group consisting of one or more diluents, one or more disintegrants, one or more disintegrant aids, one or more lubricants, one or more glidants; and optionally less than about 5% by weight of one or more film coating agents.

In some embodiments, the tablet comprises: about 20%, about 21%, about 22%, about 23%, about 24%, about 25%, about 26%, about 27%, about 28%, about 29%, about 30%, about 31%, about 32%, about 33%, about 34%, or about 35% by weight of a spray dried dispersion of 3-[4-(4-amino-piperidin-1-yl)-3-(3,5-difluoro-phenyl)-quinolin-6-yl]-2-hydroxy-benzonitrile monohydrochloride, or solvate thereof, dispersed in a polymer matrix formed from a pharmaceutically acceptable polymer; wherein the spray dried dispersion comprises an about 15/85 or about 35/65 ratio of 3-[4-(4-amino-piperidin-1-yl)-3-(3,5-difluoro-phenyl)-quinolin-6-yl]-2-hydroxy-benzonitrile monohydrochloride, or solvate thereof to a polymer matrix of hydroxypropyl methyl cellulose acetate succinate (HPMCAS), or polyvinylpyrrolidone polyvinyl acetate copolymers (PVP/VA); about 60% by weight to about 80% by weight of one or more pharmaceutical acceptable ingredients selected from the group consisting of microcrystalline cellulose, mannitol, pregelatinized starch, croscarmellose sodium, crospovidone, sodium chloride, 1:1 sodium chloride:potassium chloride, silicon dioxide, and magnesium stearate; optionally less than about 5% by weight of one or more film coating agents.

In some embodiments, the tablet comprises about 5 mg, about 10 mg, about 20 mg, about 40 mg, about 60 mg or about 80 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 10 mg, about 20 mg, about 30 mg, about 40 mg, about 50 mg, about 60 mg, about 70 mg, or about 80 mg of 3-[4-(4-amino-piperidin-1-yl)-3-(3,5-difluoro-phenyl)-quinolin-6-yl]-2-hydroxy-benzonitrile monohydrochloride, or solvate thereof.

In some embodiments, the tablet comprises about 10 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 20 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 30 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 40 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 50 mg of 3-[4-(4-amino-piperidin-1-yl)-3-(3,5-difluoro-phenyl)-quinolin-6-yl]-2-hydroxy-benzonitrile monohydrochloride, or solvate thereof. In some embodiments, the tablet comprises about 60 mg of 3-[4-(4-amino-piperidin-1-yl)-3-(3,5-difluoro-phenyl)-quinolin-6-yl]-2-hydroxy-benzonitrile monohydrochloride, or solvate thereof.

In one aspect, described herein is a method of treating acromegaly or neuroendocrine tumors, or both, in a human comprising orally administering to the human with acromegaly or neuroendocrine tumors any one of the spray-dired dispersion tablets described herein.

In some embodiments, the tablet is administered once daily. In some embodiments, the tablet is administered at least 30 minutes before a meal. In some embodiments, the tablet is administered at least 60 minutes before a meal. In some embodiments, the tablet is administered with a glass of water on an empty stomach at least 30 minutes before a meal. In some embodiments, the bioavailability of 3-[4-(4-amino-piperidin-1-yl)-3-(3,5-difluoro-phenyl)-quinolin-6-yl]-2-hydroxy-benzonitrile monohydrochloride, or solvate thereof, from the tablet is not substatntially affected by the coadministration of proton pump inhibitors, histamine H2-receptor antagonists, or antacids.

Other features and advantages of the compositions, compounds, and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
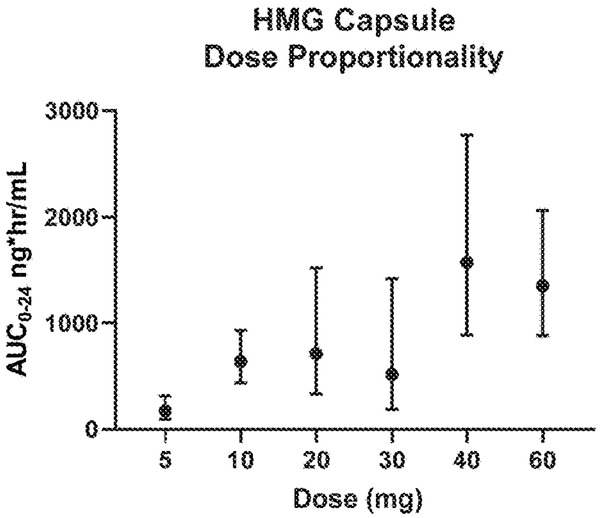
FIG. 1. Illustrates the observed dose proportionality in humans administered the HMG capsule formulation or the SDD tablet formulation of Compound A-HCl.
Figure 1:
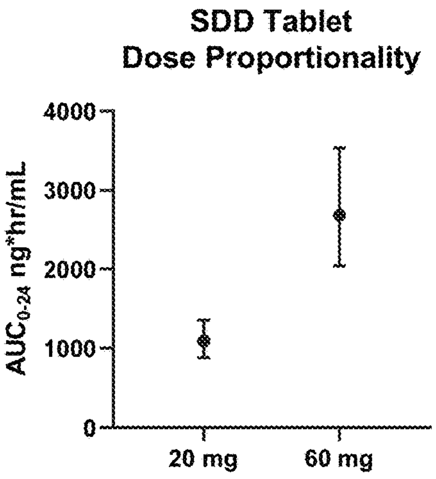

Somatostatin (SST), also known as somatotropin release inhibiting factor (SRIF) was initially isolated as a 14-amino acid peptide from ovine hypothalamus (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous sstem (CNS) and gut, and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the G protein-coupled receptor (GPCR) superfamily. SST2A receptor is the most widely expressed subtype in human tumors and is the dominant receptor by which GH secretion is suppressed. Unless otherwise stated, the term SSTR2 means SSTR2a.

It is possible to selectively modulate any one of the somatostatin receptor subtypes, or combination thereof. In some embodiments, selectively modulating any one of the somatostatin receptor subtypes relative to the other somatostatin receptor subtypes, or combination thereof, is useful in a variety of clinical applications. In some embodiments, selectively modulating any one of the somatostatin receptor subtypes relative to the other somatostatin receptor subtypes reduces unwanted side effects in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR3 agonists inhibit insulin secretion. In some embodiments, SSTR4 agonists exhibit anti-inflammatory and anti-nociceptive effects. In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cebrebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminshed in the hippocampi of Alzheimer's and Parkinson's patients, suggesting that restoration of its signaling as a potential drug target for neurodegeneration.

In one aspect, the compound 3-[4-(4-amino-piperidin-1-yl)-3-(3,5-difluoro-phenyl)-quinolin-6-yl]-2-hydroxy-benzonitrile monohydrochloride, or solvate thereof, is a selective nonpeptide SST2 biased agonist that is amenable to oral administration to a mammal in need of treatment with a somatostatin modulator.

In some embodiments, the somatostatin receptor modulator described herein has utility over a wide range of therapeutic applications. In some embodiments, the somatostatin receptor modulator described herein is used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, the somatostatin receptor modulator described herein is used in the treatment of acromegaly, neuroendocrine tumors, or both in a mammal. In some embodiments, the somatostatin receptor modulator described herein is used in the treatment of acromegaly in a mammal. In some embodiments, the somatostatin receptor modulator described herein is used in the treatment of neuroendocrine tumors.

In some embodiments, the somatostatin receptor modulator described herein inhibits the secretion of various hormones and trophic factors in mammals. In some embodiments, the somatostatin receptor modulator described herein is used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VIPomas, insulinomas and glucagonomas; or diabetes and diabetes-related pathologies, including retinopathy, neuropathy and nephropathy. In some embodiments, the somatostatin receptor modulator described herein is used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, the somatostatin receptor modulator described herein is used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, the somatostatin receptor modulator described herein provides cytoprotection in disorders involving the splanchnic blood flow, including cirrhosis and oesophagal varices.

Compound A is a somatostatin modulator that is useful in the methods of treatment described herein.

Compound A

As used herein, Compound A refers to 3-(4-(4-amino-piperidin-1-yl)-3-(3,5-difluoro-phenyl)-quinolin-6-yl)-2-hydroxy-benzonitrile, which has the chemical structure shown below.

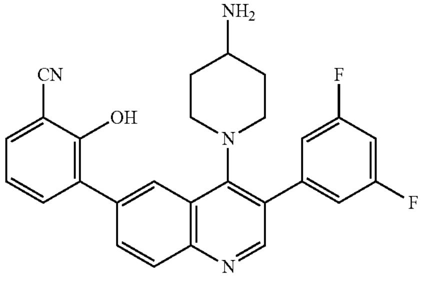 [SMILES: N#Cc1cccc(-c2ccc3ncc(-c4cc(F)cc(F)c4)c(N4CCC(N)CC4)c3c2)c1O]

Compound A is a selective nonpeptide SST2 biased agonist. In clinical studies, Compound A was shown to have an estimated bioavailability of about 70% and an observed half life of about 42 to about 50 hours. In some embodiments, Compound A is used to treat acromegaly, neuroendocrine tumors, or both. In some embodiments, Compound A is used to treat acromegaly. In some embodiments, Compound A is used to treat neuroendocrine tumors.

In some embodiments, the free base form of Compound A is incorporated into the formulations described herein. In some embodiments, Compound A is incorporated into the formulations described herein as a pharmaceutically acceptable salt. In some embodiments, Compound A is incorporated into the formulations described herein as a pharmaceutically acceptable solvate.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound disclosed herein with an acid. In some embodiments, the compound disclosed herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, Compound A is incorporated into the formulations described herein as a pharmaceutically acceptable salt form that is selected from Compound A hydrochloride and Compound A methanesulfonic acid. In some embodiments, the Compound A salt form is Compound A monohydrochloride. In some embodiments, the Compound A salt form is Compound A dihydrochloride. In some embodiments, the Compound A salt form is Compound A monomethanesulfonic acid. In some embodiments, the Compound A salt form is Compound A dimethanesulfonic acid.

In one aspect, Compound A monohydrochloride (Compound A-HCl) is incorporated into the pharmaceutical compositions described herein. Compound A monohydrochloride (Compound A-HCl), also known as 3-[4-(4-amino-piperidin-1-yl)-3-(3,5-difluoro-phenyl)-quinolin-6-yl]-2-hydroxy-benzonitrile monohydrochloride, has the following structure:

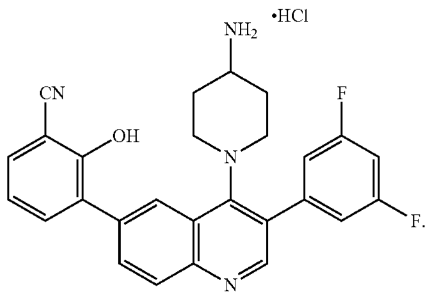 [SMILES: Cl ; N#Cc1cccc(-c2ccc3ncc(-c4cc(F)cc(F)c4)c(N4CCC(N)CC4)c3c2)c1O]

In some embodiments, the Compound A salt form is amorphous. In some embodiments, Compound A monohydrochloride is amorphous In some embodiments, the Compound A salt form is crystalline. In some embodiments, Compound A monohydrochloride is crystalline.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In most cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound A-HCl include a residual amount of an organic solvent(s). In some embodiments, compositions comprising Compound A-HCl comprise a residual amount of a Class 2 or Class 3 solvent. In some embodiments, compositions comprising Compound A-HCl comprise a residual amount of a solvent selected from ethyl acetate, isopropyl acetate, tert-butylmethylether, heptane, isopropanol, methanol, acetone, dimethylformamide, tetrahydrofuran, 1,4-dioxane, 2-methyltetrahydrofuran, toluene, and ethanol.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes of administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound disclosed herein, or a pharmaceutically acceptable salt thereof, and a co-agent, are both administered to a patient simultaneously in the form of a single entity or dosage. The term "non-fixed combination" means that the active ingredients, e.g. a compound disclosed herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats;

laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral) administration, although the most suitable route may depend upon for example the condition and disorder of the recipient.

In some embodiments, pharmaceutical compositions suitable for oral administration are presented as discrete units such as capsules or tablets each containing a predetermined amount of the active ingredient; or as a powder or granules.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets for identification or to characterize different combinations of active compound doses.

Conventional techniques to manufacture solid oral dosage forms include, but are not limited to, one or a combination of methods: (1) dry mixing, (2) direct compression, (3) milling, (4) dry or non-aqueous granulation, or (5) wet granulation. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

It should be understood that in addition to the ingredients particularly mentioned above, the compounds and compositions described herein may include other agents conventional in the art having regard to the type of formulation in question, for example those suitable for oral administration may include flavoring agents.

Provided herein are tablets comprising Compound A, or a pharmaceutically acceptable salt thereof. In some embodiments, the tablet comprises: Compound A-HCl, or solvate thereof, dispersed in a polymer matrix formed from a pharmaceutically acceptable polymer; one or more pharmaceutical acceptable ingredients selected from the group consisting of one or more diluents, one or more disintegrants, one or more lubricants, one or more glidants; and optionally one or more film coating agents.

In some embodiments, described herein is a spray-dried solid dispersion comprising (a) Compound A-HCl, or solvate thereof; and (b) a pharmaceutically acceptable polymer; wherein Compound A-HCl, or solvate thereof, is dispersed in a polymer matrix formed from the pharmaceutically acceptable polymer.

In some embodiments, described herein are tablets prepared with the spray-dried solid dispersions described herein.

Spray-Dried Solid Dispersion (SDD)

The amorphous state for most small molecule drugs is thermodynamically unstable and, unless the glass transition temperature (Tg) is sufficiently high, also kinetically unstable. However, the amorphous state can be stabilized by dilution of the drug in an excipient matrix. When an amorphous molecule is dispersed in a high Tg matrix, low molecular mobility provides a diffusion barrier which inhibits its molecular mobility that is required for phase separation upon storage. Phase separation into drug rich domains is the precursor to forming crystal nuclei and eventually widespread crystallization which results in a lost solubility advantage. In some embodiments, pharmaceutically acceptable polymers for use in preparing spray-dried solid dispersions are polymers with a high Tg. In cases when the active pharmaceutical ingredient (API) and excipient are not thermodynamically miscible with one another in the solid state, the spray-dried dispersion (SDD) is formulated such that the resulting Tg of the mixture, including absorbed water, is at least 10° C. to 20° C. greater than typical storage conditions. Further, considerations must be made with respect to water uptake during storage, either through selection of a non-hygroscopic polymer or packaging configuration, as adsorbed water will plasticize the dispersion and lower the Tg.

In some embodiments, Compound A-HCl, or solvate thereof, in the spray-dried solid dispersions described herein is substantially amorphous.

In some embodiments, the pharmaceutically acceptable polymer comprises polymers of: cellulose optionally functionalized with any combination of alkyl ethers, alkyl esters, phthalate esters; vinyl alcohol; vinyl acetate; propylene glycol; pyrrolidone; vinylpyrrolidone, oxyethylene; oxypropylene; methacrylic acid; methyl methacrylate; ethylene glycol; ethylene glycol glycerides; ethylene oxide; propylene oxide; 2-ethyl-2-oxazoline; maleic acid; methyl vinyl ether; vinyl caprolactam; or combinations thereof.

In some embodiments, the pharmaceutically acceptable polymer is hydroxypropyl methylcellulose (HPMC), hydroxypropyl methyl cellulose acetate succinate (HPMCAS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyvinylpyrrolidone polyvinyl acetate copolymers (PVP/VA), polyethylene polyvinyl alcohol copolymers, polyoxyethylene-polyoxypropylene block copolymers, cellulose acetate phthalate (CAP), hydroxypropyl methyl-cellulose phthalate (HPMCP), co-polymerc of methacrylic acid and methyl methacrylate, polyethylene glycol glycerides composed of mono-, di- and triglycerides and mono- and diesters of polyethylene glycol, hydroxypropylcellulose, copolymers of ethylene oxide and propylene oxide blocks, poly(2-ethyl-2-oxazoline), poly(maleic acid/methyl vinyl ether), polyvinyl caprolactam-polyvinyl acetate-polyethylene glycol graft copolymer, ethylene oxide/propylene oxide tetra functional block copolymer, d-alpha tocopheryl polyethylene glycol 1000 succinate, or combinations thereof.

In some embodiments, the spray-dried dispersion further comprises a dispersion polymer. Dispersion polymers are selected from hydroxypropyl methylcellulose (HPMC), hypromellose acetate succinate (hydroxypropyl methyl cellulose acetate succinate; HPMCAS, such as HPMCAS-H, HPMCAS-L, or HPMCAS-M), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyvinylpyrrolidone polyvinyl acetate copolymers (PVP/VA), polyethylene polyvinyl alcohol copolymers, polyoxyethylene-polyoxypropylene block copolymers, and combinations thereof.

HPMCAS is a cellulosic polymer with four types of substituents semirandomly substituted on the hydroxyls: methoxy, hydroxypropyloxy, acetate, and succinate. The polymer is available in three grades: L, M and H, based on the content of acetyl and succinoyl groups (wt %) in the HPMCAS molecule. Grade L: 5-9% by weight acetate, 14-18% by weight succinate, 20-24% by weight methoxy, 5-9% by weight hydroxypropyloxy. Grade M: 7-11% by weight acetate, 10-14% by weight succinate, 21-25% by weight methoxy, 5-9% by weight hydroxypropyloxy. Grade H: 10-14% by weight acetate, 4-8% by weight succinate, 22-26% by weight methoxy, 6-10% by weight hydroxypropyloxy.

In some embodiments, the pharmaceutically acceptable polymer is selected from PVP/VA 64, PVP 30, HPMCAS-L, HPMCAS-M, HPMCAS-H, Eudragit L100-55, poly(methacrylic acid-co-methyl methacrylate) (PMMAMA, or trade name Eudragit L100), Eudragit EPO, HPMC E15, HPMC E3, HPMC E5, HPMCP-HP55, and Soluplus.

In some embodiments, the pharmaceutically acceptable polymer is selected from PVP/VA 64 and HPMCAS-M. In some embodiments, the pharmaceutically acceptable polymer is PVP/VA 64. In some embodiments, the pharmaceutically acceptable polymer is HPMCAS-M.

In some embodiments, the weight ratio of Compound A-HCl, or solvate thereof, to the dispersion polymer is between about 1:10 and about 10:1. In some embodiments, the weight ratio of Compound A-HCl, or solvate thereof, to the dispersion polymer is between about 1:1 and about 1:10. In some embodiments, the weight ratio of Compound A-HCl, or solvate thereof, to the dispersion polymer is between about 1:3 and about 1:8. In some embodiments, the weight ratio of Compound A-HCl, or solvate thereof, to the dispersion polymer is between about 1:4 and about 1:7. In some embodiments, the weight ratio of Compound A-HCl, or solvate thereof, to the dispersion polymer is between about 1:4 and about 1:6. In some embodiments, the weight ratio of Compound A-HCl, or solvate thereof, to the dispersion polymer is between about 1:5 and about 1:6. In some embodiments, the weight ratio of Compound A-HCl, or solvate thereof, to the dispersion polymer is about 1:10. In some embodiments, the weight ratio of Compound A-HCl, or solvate thereof, to the dispersion polymer is about 1:9. In some embodiments, the weight ratio of Compound A-HCl, or solvate thereof, to the dispersion polymer is about 1:8. In some embodiments, the weight ratio of Compound A-HCl, or solvate thereof, to the dispersion polymer is about 1:7. In some embodiments, the weight ratio of Compound A-HCl, or solvate thereof, to the dispersion polymer is about 1:6. In some embodiments, the weight ratio of Compound A-HCl, or solvate thereof, to the dispersion polymer is about 1:5. In some embodiments, the weight ratio of Compound A-HCl, or solvate thereof, to the dispersion polymer is about 1:4. In some embodiments, the weight ratio of Compound A-HCl, or solvate thereof, to the dispersion polymer is about 1:3. In some embodiments, the weight ratio of Compound A-HCl, or solvate thereof, to the dispersion polymer is about 1:2. In some embodiments, the weight ratio of Compound A-HCl, or solvate thereof, to the dispersion polymer is about 1:1.

In some embodiments, the spray-dried solid dispersion comprises at least 5% by weight of Compound A-HCl, or solvate thereof. In some embodiments, the spray-dried solid dispersion comprises at least 10% by weight of Compound A-HCl, or solvate thereof. In some embodiments, the spray-dried solid dispersion comprises at least 15% by weight of Compound A-HCl, or solvate thereof. In some embodiments, the spray-dried solid dispersion comprises at least 20% by weight of Compound A-HCl, or solvate thereof. In some embodiments, the spray-dried solid dispersion comprises at least 25% by weight of Compound A-HCl, or solvate thereof. The % amounts are calculated based on the free base, i.e. Compound A.

In some embodiments, the spray-dried solid dispersion comprises about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of Compound A-HCl, or solvate thereof. In some embodiments, the spray-dried solid dispersion comprises about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35% by weight of Compound A-HCl, or solvate thereof. In some embodiments, the spray-dried solid dispersion comprises about 15% of Compound A-HCl, or solvate thereof. In some embodiments, the spray-dried solid dispersion comprises about 35% of Compound A-HCl, or solvate thereof. The % amounts are calculated based on the free base, i.e. Compound A.

In some embodiments, the spray-dried solid dispersion comprises about 5% by weight of Compound A-HCl, or solvate thereof. In some embodiments, the spray-dried solid dispersion comprises about 6% by weight of Compound A-HCl, or solvate thereof. In some embodiments, the spray-dried solid dispersion comprises about 7% by weight of Compound A-HCl, or solvate thereof. In some embodiments, the spray-dried solid dispersion comprises about 8% by weight of Compound A-HCl, or solvate thereof. In some embodiments, the spray-dried solid dispersion comprises about 9% by weight of Compound A-HCl, or solvate thereof. In some embodiments, the spray-dried solid dispersion comprises about 10% by weight of Compound A-HCl, or solvate thereof. In some embodiments, the spray-dried solid dispersion comprises about 11% by weight of Compound A-HCl, or solvate thereof. In some embodiments, the spray-dried solid dispersion comprises about 12% by weight of Compound A-HCl, or solvate thereof. In some embodiments, the spray-dried solid dispersion comprises about 13% by weight of Compound A-HCl, or solvate thereof. In some embodiments, the spray-dried solid dispersion comprises about 14% by weight of Compound A-HCl, or solvate thereof. In some embodiments, the spray-dried solid dispersion comprises about 15% by weight of Compound A-HCl, or solvate thereof. In some embodiments, the spray-dried solid dispersion comprises about 16% by weight of Compound A-HCl, or solvate thereof. In some embodiments, the spray-dried solid dispersion comprises about 17% by weight of Compound A-HCl, or solvate thereof. In some embodiments, the spray-dried solid dispersion comprises about 18% by weight of Compound A-HCl, or solvate thereof. In some embodiments, the spray-dried solid dispersion comprises about 19% by weight of Compound A-HCl, or solvate thereof. In some embodiments, the spray-dried solid dispersion comprises about 20% by weight of Compound A-HCl, or solvate thereof. In some embodiments, the spray-dried solid dispersion comprises about 21% by weight of Compound A-HCl, or solvate thereof. In some embodiments, the spray-dried solid dispersion comprises about 22% by weight of Compound A-HCl, or solvate thereof. In some embodiments, the spray-dried solid dispersion comprises about 23% by weight of Compound A-HCl, or solvate thereof. In some embodiments, the spray-dried solid dispersion comprises about 24% by weight of Compound A-HCl, or solvate thereof. In some embodiments, the spray-dried solid dispersion comprises about 25% by weight of Compound A-HCl, or solvate thereof. In some embodiments, the spray-dried solid dispersion comprises about 25% by weight of Compound A-HCl, or solvate thereof. In some embodiments, the spray-dried solid dispersion comprises about 27% by weight of Compound A-HCl, or solvate thereof. In some embodiments, the spray-dried solid dispersion comprises about 28% by weight of Compound A-HCl, or solvate thereof. In some embodiments, the spray-dried solid dispersion comprises about 29% by weight of Compound A-HCl, or solvate thereof. In some embodiments, the spray-dried solid dispersion comprises about 30% by weight of Compound A-HCl, or solvate thereof. In some embodiments, the spray-dried solid dispersion comprises about 31% by weight of Compound A-HCl, or solvate thereof. In some embodiments, the spray-dried solid dispersion comprises about 32% by weight of Compound A-HCl, or solvate thereof. In some embodiments, the spray-dried solid dispersion comprises about 33% by weight of Compound A-HCl, or solvate thereof. In some embodiments, the spray-dried solid dispersion comprises about 34% by weight of Compound A-HCl, or solvate thereof. In some embodiments, the spray-dried solid dispersion comprises about 35% by weight of Compound A-HCl, or solvate thereof. The % amounts are calculated based on the free base, i.e. Compound A.

In some embodiments, the spray-dried solid dispersion further comprises a non-aqueous solvent. In some embodiments, the non-aqueous solvent is present in detectable amounts. In some embodiments, the spray-dried solid dispersion is non-aqueous solvent free.

In some embodiments, the spray-dried solid dispersion further comprises a non-aqueous solvent selected from the group consisting of tert-butanol, n-propanol, n-butanol, isopropanol, ethanol, methanol, acetone, ethyl acetate, acetonitrile, methyl ethyl ketone, methyl isobutyl ketone, methyl acetate, and mixtures thereof. In some embodiments, the spray-dried solid dispersion further comprises a non-aqueous solvent selected from the group consisting of methanol, acetone, and mixtures thereof. In some embodiments, the spray-dried solid dispersion further comprises methanol.

Tablets

In one aspect, described herein is a tablet comprising: Compound A-HCl, or solvate thereof, dispersed in a polymer matrix formed from a pharmaceutically acceptable polymer; one or more pharmaceutical acceptable ingredients selected from the group consisting of one or more diluents, one or more disintegrants, one or more lubricants, one or more glidants; and optionally one or more film coating agents.

In some embodiments, Compound A-HCl, or solvate thereof, dispersed in a polymer matrix formed from a pharmaceutically acceptable polymer is the spray-dried solid dispersion described herein.

In some embodiments, tablets comprise about 2% by weight to about 20% by weight of Compound A-HCl, or solvate thereof. In some embodiments, tablets comprise about 2% by weight to about 15% by weight of Compound A-HCl, or solvate thereof.

In some embodiments, tablets comprise about 10% by weight to about 30% by weight of the polymer matrix formed from the pharmaceutically acceptable polymer. In some embodiments, tablets comprise about 20% by weight to about 35% by weight of the polymer matrix formed from the pharmaceutically acceptable polymer.

In some embodiments, tablets comprise about 2% by weight to about 10% by weight of Compound A-HCl, or solvate thereof, dispersed in about 10% by weight to about 30% by weight of a polymer matrix formed from a pharmaceutically acceptable polymer.

In some embodiments, tablets comprise about 2% by weight to about 10% by weight of Compound A-HCl, or solvate thereof, dispersed in about 10% by weight to about 30% by weight of a polymer matrix formed from a pharmaceutically acceptable polymer; about 40% by weight to about 80% by weight of one or more pharmaceutical acceptable ingredients selected from the group consisting of one or more diluents, one or more disintegrants, one or more lubricants, one or more glidants; and optionally less than about 5% by weight of one or more film coating agents.

In some embodiments, in addition to the spray-dried solid dispersion, additional excipients in the tablets comprise one or more diluents, one or more disintegrants, one or more lubricants, one or more glidants, or any combination thereof. In some embodiments, in addition to the spray-dried solid dispersion, additional excipients in the tablets comprise microcrystalline cellulose, mannitol, crospovidone, colloidal silicon dioxide, and magnesium stearate.

In some embodiments, the tablet comprises one or more fillers/binders/diluents. Fillers/binders/diluents are selected from celluloses (such as microcrystalline cellulose, carboxymethylcellulose, ethyl cellulose and methyl cellulose), starch, gelatin, sugars (such as sucrose, glucose, dextrose, mannitol, and lactose), natural and synthetic gums (such as acacia, sodium alginate, panwar gum, and ghatti gum), polyvinylpyrrolidinone, polyethylene glycol, waxes, and any combinations thereof. In some embodiments, tablets comprise microcrystalline cellulose, and mannitol.

In some embodiments, the one or more fillers/binders/diluents in the tablets described herein comprise between about 20% and about 80% by weight of the total tablet weight. In some embodiments, the one or more fillers/binders/diluents in the tablets described herein comprise between about 40% and about 65% by weight of the total tablet weight. In some embodiments, the one or more fillers/binders/diluents in the tablets described herein comprise between about 50% and about 65% by weight of the total tablet weight. In some embodiments, the one or more fillers/binders/diluents in the tablets described herein comprise about 45%, about 50%, about 55%, about 60%, about 65%, or about 70% by weight of the total tablet weight. In some embodiments, the one or more fillers/binders/diluents in the tablets described herein comprise about 58% by weight of the total tablet weight. In some embodiments, less than 70% by weight, less than 65% by weight, less than 60% by weight, less than 55% by weight, or less than 50% by weight of the total tablet weight comprise one or more fillers/binders/diluents. In some embodiments, less than 60% by weight of the total tablet weight comprise one or more fillers/binders/diluents.

In some embodiments, tablets comprise one or more disintegrants. Disintegrants are selected from croscarmellose sodium, crospovidone, sodium starch glycolate, veegum HV, methylcellulose, agar, bentonite, cellulose, carboxymethyl cellulose, and any combination thereof. In some embodiments, tablets comprise crospovidone.

In some embodiments, the one or more disintegrants in the tablets described herein comprise between about 2% and about 30% by weight of the total tablet weight. In some embodiments, the one or more disintegrants in the tablets described herein comprise between about 5% and about 20% by weight of the total tablet weight. In some embodiments, the one or more disintegrants in the tablets described herein comprise between about 10% and about 20% by weight of the total tablet weight. In some embodiments, the one or more disintegrants in the tablets described herein comprise about 5%, about 6%, about 7%, about 8%, about 9%, about 10%, about 11%, about 12%, about 13%, about 14%, about 15%, about 16%, about 17%, about 18%, about 19%, or about 20% by weight of the total tablet weight. In some embodiments, the one or more disintegrants in the tablets described herein comprise about 15% by weight of the total tablet weight. In some embodiments, less than 20% by weight of the total tablet weight comprise one or more disintegrants.

In some embodiments, tablets comprise one or more lubricants. Lubricants are selected from talc, magnesium stearate, calcium stearate, stearic acid, sodium stearyl fumarate, glyceryl behenate, hydrogenated vegetable oils, polyethylene glycol, and any combinations thereof. In some embodiments, tablets comprise magnesium stearate.

In some embodiments, the one or more lubricants in the tablets described herein comprise between about 0.1% and about 5% by weight of the total tablet weight. In some embodiments, the one or more lubricants in the tablets described herein comprise between about 0.1% and about 2% by weight of the total tablet weight. In some embodiments, the one or more lubricants in the tablets described herein comprise between about 0.1% and about 1% by weight of the total tablet weight. In some embodiments, the one or more lubricants in the tablets described herein comprise about 0.1%, about 0.2%, about 0.3%, about 0.4%, about 0.5%, about 0.6%, about 0.7%, about 0.8%, about 0.9%, or about 1% by weight of the total tablet weight. In some embodiments, the one or more lubricants in the tablets described herein comprise about 0.5% by weight of the total tablet weight. In some embodiments, less than 2% by weight of the total tablet weight comprise one or more lubricants. In some embodiments, less than 1% by weight of the total tablet weight comprise one or more lubricants.

In some embodiments, tablets comprise one or more glidants. A glidant is a substance that is added to a powder to improve its flowability. Examples of glidants include magnesium stearate, colloidal silicon dioxide, starch and talc. In some embodiments, tablets comprise colloidal silicon dioxide.

In some embodiments, the one or more lubricants in the tablets described herein comprise between about 0.1% and about 5% by weight of the total tablet weight. In some embodiments, the one or more lubricants in the tablets described herein comprise between about 0.1% and about 2% by weight of the total tablet weight. In some embodiments, the one or more lubricants in the tablets described herein comprise between about 0.5% and about 1.5% by weight of the total tablet weight. In some embodiments, the one or more lubricants in the tablets described herein comprise about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2% by weight of the total tablet weight. In some embodiments, the one or more lubricants in the tablets described herein comprise about 1% by weight of the total tablet weight. In some embodiments, less than 2% by weight of the total tablet weight comprise one or more lubricants. In some embodiments, less than 1.5% by weight of the total tablet weight comprise one or more lubricants.

Additional Excipients

In some embodiments, the tablet described herein comprises additional excipients including, but not limited, to buffering agents, glidants, preservatives, and coloring agents. Additional excipients such as bulking agents, tonicity agents, and chelating agents are within the scope of the embodiments.

Non-limiting examples of buffering agents include, but are not limited to, sodium bicarbonate, potassium bicarbonate, magnesium hydroxide, magnesium lactate, magnesium glucomate, aluminum hydroxide, aluminum hydroxide/sodium bicarbonate co precipitate, a mixture of an amino acid and a buffer, a mixture of aluminum glycinate and a buffer, a mixture of an acid salt of an amino acid and a buffer, and a mixture of an alkali salt of an amino acid and a buffer.

Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

In some embodiments, the tablet described herein comprises a preservative. Preservatives include anti-microbials, anti-oxidants, and agents that enhance sterility. Exemplary preservatives include ascorbic acid, ascorbyl palmitate, BHA, BHT, citric acid, erythorbic acid, fumaric acid, malic acid, propyl gallate, sodium ascorbate, sodium bisulfate, sodium metabisulfite, sodium sulfite, parabens (methyl-, ethyl-, butyl-), benzoic acid, potassium sorbate, vanillin, and the like.

In some embodiments, the tablet described herein comprises a coloring agent for identity and/or aesthetic purposes of the resultant liquid form. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

Additional excipients are contemplated in the tablet embodiments. These additional excipients are selected based on function and compatibility with the tablet compositions described herein and may be found, for example in *Remington: The Science and Practice of Pharmacy*, Nineteenth Ed (Easton, PA: Mack Publishing Company, 1995); Hoover, John E., *Remington's Pharmaceutical Sciences*, (Easton, PA: Mack Publishing Co 1975); Liberman, H. A. and Lachman, L., Eds., *Pharmaceutical Dosage Forms* (New York, NY: Marcel Decker 1980); and *Pharmaceutical Dosage Forms and Drug Delivery Systems*, Seventh Ed (Lippincott Williams & Wilkins 1999), herein incorporated by reference in their entirety.

In further embodiments, the tablets described herein are coated tablets, such as enteric-coated tablets, sugar-coated, or film-coated tablets.

In one embodiment, the individual unit dosages also include film coatings, which disintegrate upon oral ingestion or upon contact with diluent. In one embodiment, these formulations are manufactured by conventional techniques.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are film-coated tablets forms, which comprise: a combination of an active ingredient (e.g. Compound A-HCl) and one or more tabletting excipients to form a tablet core and subsequently coating the core. The tablet cores are produced using conventional tabletting processes and with subsequent compression and coating.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In some embodiments, tablets are coated with water soluble, pH independent film coating which allows for immediate disintegration for fast, active release (e.g. Opadry products).

Dosage in the Tablet

In some embodiments, the amount of Compound A-HCl, or solvate thereof, in the tablet is between about 5 mg and about 100 mg. In some embodiments, the amount of Compound A-HCl, or solvate thereof, in the tablet is between about 5 mg and about 80 mg. In some embodiments, the amount of Compound A-HCl, or solvate thereof, in the tablet is between about 5 mg and about 60 mg. In some embodiments, the amount of Compound A-HCl, or solvate thereof, in the tablet is between about 10 mg and about 40 mg.

In some embodiments, the amount of Compound A-HCl, or solvate thereof, in the tablet is about 10 mg. In some embodiments, the amount of Compound A-HCl, or solvate thereof, in the tablet is about 20 mg. In some embodiments, the amount of Compound A-HCl, or solvate thereof, in the tablet is about 30 mg. In some embodiments, the amount of Compound A-HCl, or solvate thereof, in the tablet is about 40 mg. In some embodiments, the amount of Compound A-HCl, or solvate thereof, in the tablet is about 50 mg. In some embodiments, the amount of Compound A-HCl, or solvate thereof, in the tablet is about 60 mg. In some embodiments, the amount of Compound A-HCl, or solvate thereof, in the tablet is about 70 mg. In some embodiments, the amount of Compound A-HCl, or solvate thereof, in the tablet is about 80 mg.

Methods of Dosing and Treatment Regimens

In one embodiment, the pharmaceutical compositions disclosed herein are used as medicaments for the treatment of diseases or conditions in a mammal that would benefit from modulation of somatostatin activity. Methods for treating any of the diseases or conditions described herein in a mammal in need of such treatment, involves administration of pharmaceutical compositions that include Compound A, or a pharmaceutically acceptable salt thereof, in therapeutically effective amounts to said mammal.

In certain embodiments, the compositions containing Compound A described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In general, however, doses employed for adult human treatment are typically in the range of about 10 mg to about 100 mg per day of Compound A. In one embodiment, the desired dose is conveniently presented in a single dose or in divided doses administered simultaneously or at appropriate intervals, for example as two, three, four or more sub-doses per day.

In any of the aforementioned aspects are further embodiments comprising single administrations of the effective amount of the compound, including further embodiments in which the compound is administered once a day.

EXAMPLES

The following examples are provided for illustrative purposes only and not to limit the scope of the claims provided herein.

Example 1

Oral Capsules

Representative capsules are described below in Table 1.

TABLE 1

| Component Name | Function | Quantity per Unit (mg) | % w/w |
|---|---|---|---|
| Compound A-HCl[a] | Drug substance | 10.00 | 5.00 |
| Microcrystalline Cellulose | Diluent | 85.5 | 42.77 |
| Mannitol | Diluent | 85.5 | 42.77 |
| Croscarmellose Sodium | Disintegrant | 7.4 | 3.70 |
| Vitamin E Polyethylene Glycol Succinate (TPGS) | Solubilizer | 8.5 | 4.27 |
| Colloidal Silicon Dioxide | Glidant | 2.0 | 1.00 |
| Sodium Stearyl Fumarate | Lubricant | 1.0 | 0.50 |
| Size 2 Gelatin Capsule[c] | Capsule Shell | NA | NA |
| Total | | 200.00[b] | 100.00 |

[a]Amount corrected for assay and moisture, chloride and isopropyl alcohol content;
[b]Capsule fill weight adjusted based upon blend assay;
[c]Composed of red iron oxide, titanium dioxide and gelatin.

A representative description of the manufacturing process for the hot melt granulation capsules is as follows:

Stage 1: High Shear Wet Granulation: Melt the Vitamin E Polyethylene Glycol Succinate (TPGS). Compound A-HCl, mannitol, microcrystalline cellulose, croscarmellose sodium and silicon dioxide are charged into a high shear wet granulator and mixed. The melted Vitamin E TPGS is sprayed onto the granulation components.

Stage 2: Milling: The wet granulation is milled through a screening mill using an appropriately sized screen.

Stage 3: Blending: The sodium stearyl fumarate is sieved using an appropriately sized screen. The milled granulation is charged into the diffusion mixer (tumble) along with the sodium stearyl fumarate and blended.

Stage 4: Encapsulation: The 10 mg capsules were automatically encapsulated in Size 2 gelatin capsules.

Example 2

Spray-Dried Solid Dispersions

Spray-dried solid dispersions were prepared with 15% by weight Compound A-HCl: 15/85 Compound A-HCl/HPMCAS-M and 15/85 Compound A-HCl/PVP VA64 formulations. The manufactures were completed using the BLD-150, the Bend Lab Dryer with 150 kg/hr drying gas capacity. The parameters varied were solution solids loading for the HPMCAS-M SDD formulation to help reduce nozzle bearding, and dryer outlet temperature for the PVP VA64 SDD to de-risk fluctuations that may occur during clinical manufacturing. The original process parameter screening plan specified manufacturing the decreased dryer outlet temperature condition with a larger orifice nozzle to produce larger particles, however based on the results of the first spray it was determined that the atomization pressure needed to achieve the desired solution flow rate would have been too low to fully atomize the solution with the larger orifice. As dryer outlet temperature tends to have more variability than solution flow rate, the parameter screen was shifted to focus on de-risking the dryer outlet temperature alone while ensuring fully atomized droplets. Dryer outlet temperature variation could affect residual solvent levels in the SDDs, which can affect physical and chemical stability. All sprays were completed successfully with good yields, and indicate a robust processing space for both formulations.

15/85 Compound A HPMCAS-M SDD Formulation Manufacturing Details

Three sub batches of 15/85 Compound A-HCl/HPMCAS-M SDDs were sprayed to explore the manufacture processing space and prepare for clinical trial manufacturing. A sub batch was sprayed first at 10 wt % solids, and significant nozzle bearding that appeared to affect the spray plume was observed after about 45 minutes on solution.

The solution was diluted to 8 wt %, and a sub batch was manufactured with a duration of 1 hour to ensure bearding was reduced. A very small amount of bearding was observed during this batch after about 50 minutes on solution, but did not appear to affect the atomization plume and the 8 wt % solids loading was selected.

Cooling water at 2 GPM and approximately 7° C. was run through the spray dryer lid throughout all sprays to keep the lid cool and prevent sticking and browning. No significant lid buildup or browning was seen throughout manufacturing. No cleaning was performed between sprays, and all sprays were completed from one solution with additional solvent added prior to manufacturing batches 2A and 2C. A summary of the manufacturing parameters used for all three sub batches is shown in Table 2.

TABLE 2

Manufacturing summary for 15/85 Compound A-HCl/HPMCAS-M SDDs.

| Parameter | Lot 2A | Lot 2B | Lot 2C |
|---|---|---|---|
| Bulk SDD collected (g) | 5316 | 2231 | 624 |
| Solids loading in solution (wt %) | 8 | 10 | 8 |
| Solvent | | Methanol | |
| Atomizer | | Pressure swirl: Steinen A75 | |
| Atomizing pressure (psig) | 370 | 301 | 345 |
| Solution flow (g/min) | 131 | 132 | 131 |
| Drying gas flow rate (g/min) | 1848 | 1848 | 1848 |
| Dryer inlet temperature (° C.) | 146 | 145 | 144 |
| Dryer outlet temperature (° C.) | 45 | 45 | 45 |
| Bulk secondary tray drying | 16 hours at 40° C./15% RH | 17 hours at 40° C./15% RH | |
| Dry yield (%)[1] | 96 | 96 | 93 |
| Spray duration (hours) | 8 | 3 | 1 |
| Calculated dryer relative saturation (%) | | 11 | |
| Calculated dew point (° C.) | | 3 | |

[1]Dry yield is calculated as SDD samples and dry bulk collected divided by the amount of solids sprayed.

15/85 Compound A-HCl/PVP VA64 SDD Formulation Manufacturing Details

Process parameter screening sprays and an FPN demonstration batch were also completed for the 15/85 Compound A-HCl/PVP VA64 SDD formulation. The dryer outlet temperature was varied to de-risk process parameter variability to prepare for clinical trial manufacturing.

The process space was constrained by a maximum dryer outlet temperature, the dryer outlet temperature, and the minimum desired solution flow rate. A maximum inlet temperature of 160° C. was specified to avoid sticking or browning of SDD on the spray dryer lid, and the minimum flow rate was set at 100 g/min to ensure sufficient throughput. The minimum and maximum dryer outlet temperatures were chosen to be 40° C. and 65° C. respectively to ensure adequate particle drying and that the dryer outlet temperature will not be above the wet particle Tg.

The process parameter screening sprays for the PVP VA64 formulation explored the manufacturing space by varying the dryer outlet temperature. This allowed investigation of the effect of dryer relative saturation on particle residual solvent content, morphology, density, and stability.

Cooling water was run at 2 GPM and approximately 7° C. throughout all sprays to prevent lid buildup and browning, and neither were noted. No nozzle bearding was observed throughout all three manufactures. All sprays were completed from one solution. The manufacturing details of each sub batch are summarized in Table 3.

TABLE 3

15/85 Compound A-HCl*/PVP VA64 SDD process parameters

| Parameter | Lot 4A | Lot 4B | Lot 4C |
|---|---|---|---|
| Bulk SDD collected (g) | 5285 | 623 | 624 |
| Solids loading in solution (wt %) | | 8 | |
| Solvent | | Methanol | |
| Atomizer | | Pressure swirl: Steinen A75 | |
| Atomizing pressure (psig) | 422 | 449 | 445 |
| Solution flow (g/min) | 128 | 133 | 132 |
| Drying gas flow rate (g/min) | 1845 | 1848 | 1849 |
| Dryer inlet temperature (° C.) | 143 | 153 | 132 |

TABLE 3-continued

| 15/85 Compound A-HCl*/PVP VA64 SDD process parameters | | | |
|---|---|---|---|
| Parameter | Lot 4A | Lot 4B | Lot 4C |
| Dryer outlet temperature (° C.) | 45 | 49 | 40 |
| Bulk secondary tray drying | 18 hours at 40° C./15% RH | 26 hours at 40° C./15% RH | |
| Dry yield (%)[1] | 92 | 86 | 91 |
| Spray duration (hours) | 8 | 1 | 1 |
| Calculated dryer relative saturation (%) | 11 | 9 | 14 |
| Calculated dew point (° C.) | | 3 | |

*Compound A-HCl, formulated on a basis of free base.

[1]Dry yield is calculated as SDD samples and dry bulk collected divided by the amount of solids sprayed.

SDD Characterization

Particle Properties: The particle size distribution and bulk and tapped densities were measured for each batch of Compound A-HCl SDD. The HPMCAS-M SDDs have larger particle sizes, which is expected because the HPMCAS-M solution is more viscous than the PVP VA64 solution which leads to larger droplets for a given nozzle configuration. The increased solids loading in solution of lot 2B led to larger particles than batches 2A and 2C, which is also due to the higher viscosity of the spray solution. The particle size distributions of all PVPVA-64 batches are similar, as expected.

The bulk and tapped densities of 2A and 2C are similar, while batch 2B has a slightly lower density potentially due to the larger particles. The bulk and tapped densities of all PVPVA-64 batches are similar, indicating a robust process with respect to the dryer outlet temperature effects on powder properties.

Residual Solvent and Water Content: The residual methanol and water of the six SDDs were measured using GC and KF respectively. All SDDs contained residual methanol below the ICH guideline of 0.3 wt % after secondary drying, suggesting adequate drying at 40° C./15% RH.

Morphology by SEM: The particle morphology of all six SDDs was evaluated via SEM. Each SDD showed typical morphology with no evidence of irregular particles suggesting adequate atomization for all conditions tested. The HPMCAS-M particles were primarily collapsed spheres while the PVP VA64 SDDs contain a larger fraction of spherical particles.

Crystallinity by PXRD: All six SDDs were evaluated for crystallinity using PXRD. All SDDs were amorphous by PXRD as evident in the absence of sharp diffraction peaks.

Thermal Characteristics by DSC: All six SDDs were characterized by modulated DSC. The results are tabulated in Table 4. The manufactured SDDs were all amorphous and homogenous by DSC as evident by the presence of a single glass transition in the reversing heat signal. Neither formulation shows signs of crystallization after the Tg suggesting low propensity for crystallization of Compound A at those temperatures for both formulations. Furthermore, both formulations showed high Tg relative to ambient temperatures suggesting low physical stability risks in dry conditions. Packaging to minimize humidity will be necessary for the PVP VA64 formulation.

TABLE 4

| Tabulated thermal characteristics of the six batches as measured by DSC. | | | | | |
|---|---|---|---|---|---|
| Sample | Lot | Tg (° C.) | Std Dev* | Delta Cp (J/(g*° C.)) | Std Dev* |
| 15/85 Compound A- | 2A | 135.2 | 0.35 | 0.27 | 0.03 |
| HCl/HPMCAS-M SDD | 2B | 134.7 | 0.36 | 0.25 | 0.02 |
| | 2C* | 134.5 | 0.95 | 0.26 | 0.00 |
| 15/85 Compound A- | 4A* | 125.5 | 0.04 | 0.31 | 0.01 |
| HCl/PVP VA64 SDD | 4B | 125.6 | 0.26 | 0.30 | 0.01 |
| | 4C | 125.6 | 0.17 | 0.35 | 0.08 |

*Average is from n = 2 replicates. As a result, std deviation is actually calculated as range/2.

Summary

Physical Stability observations: PVP VA64 SDD appeared to deliquesce upon storage with crystals observed at 3 months (40° C./75% RH open). Storage with desiccant is recommended. HPMCAS-M SDD was physically stable through 6 months at 40° C./75% RH open.

Chemical Stability observations: Possible acid catalyzed degradation in the HPMCAS-M formulation on stability. Some degradation in the PVP VA64 formulation as well, but not as significant as the HPMCAS-M SDD. Packaging will be required for the PVPVA SDD which will be driven by physical stability concerns.

The 15% by weight Compound A/PVP VA64 was selected as the lead SDD formulation. 12-month stability: 15% Compound A-HCl/PVP-VA64 SDD 12-month SDD samples were held at 5° C., 25° C./60% RH, and 40° C./75% RH with desiccant. Samples for water analysis by Karl Fisher titration were prepared and analyzed immediately; the remaining samples were vacuum desiccated overnight to remove residual moisture and preserve the physical state of SDD's for further characterization. A list of the analytical tests performed for characterization included: appearance, water content by Karl Fisher titration, Powder x-ray diffraction (PXRD), scanning electron microscopy (SEM), thermal characterization by modulated differential scanning calorimetry (mDSC), dissolution performance by micro-centrifuge (MCT) test, assay and related substances by HPLC.

Conclusion from PXRD analysis on the 12-month SDD stability samples: There was no evidence of crystallinity in samples stored at 12 months at each of the stability conditions.

Conclusion from SEM analysis on the 12-month SDD stability samples: No particle fusion was observed across all stability conditions at 12 month. There was no evidence of crystallinity in samples stored at 12 months at each of the stability conditions.

Conclusion from SEM analysis on the 12-month SDD stability samples: No particle fusion is observed across all stability conditions at 12 months. There was no evidence of crystallinity in samples stored at 12 months at each of the stability conditions.

Conclusions from mDSC analysis on the 12-month SDD stability samples: Repeated analysis of the 12 month SDD sample held at 5° C. affords non-reproducible thermograms, the cause for this result is not known at this time. The 5° C. sample was determined to be physically stable by all other characterization techniques. The 12 month SDD samples held at 25° C./60% RH and 40° C./75% RH showed a single, reproducible Tg at 124-125° C., supporting the conclusion that the SDD is stable after 12 months of storage with desiccant at these conditions.

Conclusion from MCT dissolution analysis on the 12-month SDD stability samples: Non-sink dissolution performance of the 12 month stability samples is consistent with the initial (to) sample stored at −20° C.

35/65 Compound A-HCV/PVP VA64 SDD Formulation Manufacturing Details

Spray-dried solid dispersions were prepared with 35% by weight Compound A-HCl: 35/65 Compound A-HCl/PVP VA64 formulation.

The manufacture of the SDD was completed using the SD-180 lab dryer. Secondary drying was completed using the Binder Convection Dryer. The manufacturing details are summarized in Table 5.

The spray was completed successfully with good yield.

TABLE 5

35/65 Compound A-HCl*/PVP VA64 SDD process parameters

| Parameter | Value |
| --- | --- |
| Bulk SDD collected (g) | 2796 |
| Solids loading in solution (wt %) | 10.8 |
| Solvent | Methanol |
| Atomizer | SD-90 with Pressure Swirl |
| Atomizing pressure (psig) | 320 |
| Solution flow (g/min) | 115 |
| Drying gas rate (acfm) | 80 |
| Dryer inlet temperature (° C.) | 100 |
| Dryer outlet temperature (° C.) | 45 |
| Condensore Setpoint (° C.) | −20 |
| Bulk secondary tray drying | 48 hours at 40° C./ambient pressure |

*Compound A-HCl, formulated on a basis of free base

Example 3

Oral Tablets

Representative 10 mg, 20 mg, 30 mg, 40 mg, and 60 mg spray-dried dispersion tablets are presented in Tables 6, 7, 8, 9, 10, 11, 12, and 13.

Typical excipients used to prepare the tablets included: microcrystalline cellulose, mannitol, crospovidone, colloidal silicon dioxide, magnesium stearate, and Opadry White 03K184116 (film coating).

TABLE 6

Representative 10 mg spray-dried dispersion tablets.

| Component Name | Function | Quantity per Unit (mg) | % w/w |
| --- | --- | --- | --- |
| Spray-Dried Dispersion | | | |
| Compound A-HCl | Drug substance | 10.00 | 3.20 |
| PVP/VA 64 | Film Forming Agent | 56.67 | 18.15 |
| Methanol[a] | Solvent | NA | NA |
| Roller Compaction/Blending | | | |
| Microcrystalline Cellulose | Diluent | 130.31 | 41.74 |
| Mannitol | Diluent | 53.04 | 16.99 |
| Crospovidone | Disintegrant | 30.29 | 9.71 |
| Colloidal Silicon Dioxide | Glidant | 1.53 | 0.49 |
| Magnesium Stearate | Lubricant | 0.76 | 0.24 |
| Blending/Compression | | | |
| Crospovidone | Disintegrant | 18.18 | 5.82 |
| Colloidal Silicon Dioxide | Glidant | 1.52 | 0.49 |
| Magnesium Stearate | Lubricant | 0.76 | 0.24 |
| Film Coating | | | |
| Opadry ® White 03K18416[b] | Film Coating Agent | 9.09 | 2.91 |
| Purified Water[c] | Solvent | NA | NA |
| Total | | 312.15 | 100.0 |

[a]Methanol removed on drying during the spray drying process.

[b]Composed of Hypromellose 2910, titanium dioxide and triacetin.

[c]Purified water removed on drying during the film coating process.

TABLE 7

Representative 20 mg spray-dried dispersion (HPMCAS-M) tablets.

| Function | Ingredient | Formulation no. A1 | A2 | A3 |
|---|---|---|---|---|
| | | Tablet Dose/ Tablet Weight (mg/mg) | | |
| | | 20/400 | 20/400 | 20/400 |
| | | % w/w of Blend | | |
| Pregranulation | | | | |
| Active | 15/85 Compound A-HCl/HPMCAS-M | 33.33% | 33.33% | 33.33% |
| Local PH Modifier | Citric Acid | — | — | 5.00% |
| Filler | Microcrystalline Cellulose (Avicel PH-102) | 38.11% | 40.11% | 36.78% |
| Filler | Mannitol (Mannogem EZ Spray Dried) | 19.06% | 20.06% | 18.39% |
| Disintegration Aid | Sodium Chloride (NaCl Powder) | — | — | — |
| Disintegrant | Sodium Starch Glycolate (Explotab) | 5.00% | — | — |
| Disintegrant | Crospovidone (PVP-XL) | — | 5.00% | 3.00% |
| Glidant | Silicon dioxide (Syloid 244 FP) | 0.50% | 0.50% | 0.50% |
| Lubricant | Magnesium Stearate | 0.25% | 0.25% | 0.25% |
| Extragranular | | | | |
| Disintegrant | Sodium Starch Glycolate (Explotab) | 3.00% | — | — |
| Disintegrant | Crospovidone (PVP-XL) | — | — | 2.00% |
| Glidant | Silicon dioxide (Syloid 244 FP) | 0.50% | 0.50% | 0.50% |
| Lubricant | Magnesium Stearate | 0.25% | 0.25% | 0.25% |

TABLE 8

Representative 20 mg spray-dried dispersion (PVPVA 64) tablets.

| Function | Ingredient | Formulation no. B1 | B2 | B3 |
|---|---|---|---|---|
| | | Tablet Dose/ Tablet Weight (mg/mg) | | |
| | | 20/400 | 20/400 | 20/400 |
| | | % w/w of Blend | | |
| Pregranulation | | | | |
| Active | 15/85 Compound A-HCl/PVPVA 64 | 33.33% | 33.33% | 33.33% |
| Local PH Modifier | Citric Acid | 5.00% | — | — |
| Filler | Microcrystalline Cellulose (Avicel PH-102) | 43.17% | 33.17% | 33.17% |
| Filler | Mannitol (Mannogem EZ Spray Dried) | — | 20.00% | — |
| Disintegration Aid | Sodium Chloride (NaCl Powder) | 5.00% | — | 20.00% |
| Disintegrant | Sodium Starch Glycolate (Explotab) | 6.00% | — | — |
| Disintegrant | Crospovidone (PVP-XL) | — | 6.00% | 6.00% |
| Glidant | Silicon dioxide (Syloid 244 FP) | 0.50% | 0.50% | 0.50% |
| Lubricant | Magnesium Stearate | 0.25% | 0.25% | 0.25% |
| Extragranular | | | | |
| Disintegrant | Sodium Starch Glycolate (Explotab) | 6.00% | — | — |
| Disintegrant | Crospovidone (PVP-XL) | — | 6.00% | 6.00% |
| Glidant | Silicon dioxide (Syloid 244 FP) | 0.50% | 0.50% | 0.50% |
| Lubricant | Magnesium Stearate | 0.25% | 0.25% | 0.25% |

TABLE 9

| Additional representative 20 mg spray dried dispersion tablets. | | | | | |
|---|---|---|---|---|---|
| | | Formulation no. | | | |
| | | A4 | B4 | B5 | B6 |
| | | Tablet Dose/ Tablet Weight (mg/mg) | | | |
| | | 20/400 | 20/606.1 | 20/400 | 20/606.1 |
| Function | Ingredient | % w/w of Blend | | | |
| Pregranulation | | | | | |
| Active | 15/85 Compound A-HCl/HPMCAS-M | 33.33% | — | — | — |
| Active | 15/85 Compound A-HCl/PVPVA 64 | — | 22.00% | 33.33% | 22.00% |
| Local PH Modifier | Citric Acid | 5.00% | 5.00% | — | — |
| Filler | Microcrystalline Cellulose (Avicel PH-102) | 35.61% | 40.50% | 33.17% | 43.00% |
| Filler | Mannitol (Mannogem EZ Spray Dried) | 16.56% | 15.00% | 16.00% | 17.50% |
| Disintegrant | Crospovidone (PVP-XL) | 5.00% | 10.00% | 10.00% | 10.00% |
| Glidant | Silicon dioxide (Syloid 244 FP) | 0.50% | 0.50% | 0.50% | 0.50% |
| Lubricant | Magnesium Stearate | 0.25% | 0.25% | 0.25% | 0.25% |
| Extragranular | | | | | |
| Disintegrant | Crospovidone (PVP-XL) | 3.00% | 6.00% | 6.00% | 6.00% |
| Glidant | Silicon dioxide (Syloid 244 FP) | 0.50% | 0.50% | 0.50% | 0.50% |
| Lubricant | Magnesium Stearate | 0.25% | 0.25% | 0.25% | 0.25% |

TABLE 10

| Representative 30 mg and 40 mg spray-dried dispersion (PVPVA 64) tablets. | | | |
|---|---|---|---|
| | | Formulation no. | |
| | | D1 | D2 |
| | | Tablet Dose/ Tablet Weight (mg/mg) | |
| | | 30/909.2 | 40/1212.3 |
| Function | Ingredient | % w/w of Blend | |
| Active | 15/85 Compound A-HCl/PVPVA 64 | 22.00 | 22.00 |
| Filler | Microcrystalline Cellulose (Avicel PH-101) | 43.00 | 43.00 |
| Filler | Mannitol (Parteck M100) | 17.50 | 17.50 |
| Disintegrant | Crospovidone (PVP-XL) | 10.00 | 10.00 |
| Glidant | Silicon dioxide (Syloid 244 FP) | 0.50 | 0.50 |
| Lubricant | Magnesium Stearate | 0.25 | 0.25 |
| Disintegrant | Crospovidone (PVP-XL) | 6.00 | 6.00 |
| Glidant | Silicon dioxide (Syloid 244 FP) | 0.50 | 0.50 |
| Lubricant | Magnesium Stearate | 0.25 | 0.25 |

TABLE 11

| Additional representative 40 mg spray-dried dispersion (PVPVA 64) tablets. | | | | |
|---|---|---|---|---|
| | | Formulation no. | | |
| | | E1 | E2 | E3 |
| | | Tablet Dose/ Tablet Weight (mg/mg) | | |
| | | 40/500 | 40/600 | 40/600 |
| Function | Ingredient | % w/w of Blend | | |
| Pregranulation | | | | |
| Active | 35/65 Compound A-HCl/PVPVA 64 | 34.29% | 28.57% | 28.57% |
| Filler | Microcrystalline Cellulose (Avicel PH-101) | 32.14% | 28.18% | 22.18% |
| Filler | Mannitol (Parteck M100) | 16.07% | 14.09% | 11.09% |
| Disintegrant | Croscarmellose Sodium (Ac-Di-Sol) | 5.00% | 5.00% | 7.81% |

TABLE 11-continued

Additional representative 40 mg spray-dried dispersion (PVPVA 64) tablets.

| Function | Ingredient | Formulation no. E1 Tablet Dose/Tablet Weight (mg/mg) 40/500 % w/w of Blend | E2 40/600 | E3 40/600 |
|---|---|---|---|---|
| Disintegrant | Crospovidone (PVP-XL) | 5.00% | 5.00% | 7.81% |
| Glidant | Silicon dioxide (Syloid 244 FP) | 0.50% | 0.50% | 0.50% |
| Lubricant | Magnesium Stearate | 0.25% | 0.25% | 0.25% |
| | Extragranular | | | |
| Filler | Microcrystalline Cellulose (Avicel PH-101) | — | 11.67% | 11.67% |
| Disintegrant | Croscarmellose Sodium (Ac-Di-Sol) | 3.00% | 3.00% | 4.69% |
| Disintegrant | Crospovidone (PVP-XL) | 3.00% | 3.00% | 4.69% |
| Glidant | Silicon dioxide (Syloid 244 FP) | 0.50% | 0.50% | 0.50% |
| Lubricant | Magnesium Stearate | 0.25% | 0.25% | 0.25% |

TABLE 12

Representative 60 mg spray-dried dispersion (PVPVA 64) tablets.

| Function | Ingredient | Formulation no. C1 Tablet Dose/Tablet Weight (mg/mg) 60/500 % w/w of Blend | C2 60/600 | C3 60/600 |
|---|---|---|---|---|
| | Pregranulation | | | |
| Active | 35/65 Compound A-HCl/PVPVA 64 | 34.29% | 28.57% | 28.57% |
| Filler | Microcrystalline Cellulose (Avicel PH-101) | 32.14% | 28.18% | 22.18% |
| Filler | Mannitol (Parteck M100) | 16.07% | 14.09% | 11.09% |
| Disintegrant | Croscarmellose Sodium (Ac-Di-Sol) | 5.00% | 5.00% | 7.81% |
| Disintegrant | Crospovidone (PVP-XL) | 5.00% | 5.00% | 7.81% |
| Glidant | Silicon dioxide (Syloid 244 FP) | 0.50% | 0.50% | 0.50% |
| Lubricant | Magnesium Stearate | 0.25% | 0.25% | 0.25% |
| | Extragranular | | | |
| Filler | Microcrystalline Cellulose (Avicel PH-101) | — | 11.67% | 11.67% |
| Disintegrant | Croscarmellose Sodium (Ac-Di-Sol) | 3.00% | 3.00% | 4.69% |
| Disintegrant | Crospovidone (PVP-XL) | 3.00% | 3.00% | 4.69% |
| Glidant | Silicon dioxide (Syloid 244 FP) | 0.50% | 0.50% | 0.50% |
| Lubricant | Magnesium Stearate | 0.25% | 0.25% | 0.25% |

TABLE 13

Additional representative 60 mg spray-dried dispersion (PVPVA 64) tablets.

| Function | Ingredient | Formulation no. C4 Tablet Dose/Tablet Weight (mg/mg) 60/600 % w/w of Blend | C5 60/600 | C6 60/600 |
|---|---|---|---|---|
| | Pregranulation | | | |
| Active | 35/65 Compound A-HCl/PVPVA 64 | 28.57% | 28.57% | 28.57% |
| Filler | Microcrystalline Cellulose (Avicel PH-101) | 15.08% | 18.41% | 18.41% |
| Filler | Mannitol (Parteck M100) | 7.54% | 9.21% | 9.21% |
| Disintegrant | Pregelatinized Starch (Starch 1500) | 20.00% | — | — |

TABLE 13-continued

Additional representative 60 mg spray-dried dispersion (PVPVA 64) tablets.

| Function | Ingredient | C4 | C5 | C6 |
|---|---|---|---|---|
| | | Formulation no. | | |
| | | Tablet Dose/ Tablet Weight (mg/mg) | | |
| | | 60/600 | 60/600 | 60/600 |
| | | % w/w of Blend | | |
| Disintegration Aid | Sodium Chloride (NaCl Powder) | — | 10.00% | — |
| Disintegration Aid | 1:1 Sodium Chloride:Potassium Chloride | — | — | 10.00% |
| Disintegrant | Croscarmellose Sodium (Ac-Di-Sol) | 5.00% | 5.00% | 5.00% |
| Disintegrant | Crospovidone (PVP-XL) | 5.00% | 5.00% | 5.00% |
| Glidant | Silicon dioxide (Syloid 244 FP) | 0.50% | 0.50% | 0.50% |
| Lubricant | Magnesium Stearate | 0.25% | 0.25% | 0.25% |
| | Extragranular | | | |
| Filler | Microcrystalline Cellulose (Avicel PH-101) | 11.31% | 11.31% | 11.31% |
| Disintegrant | Croscarmellose Sodium (Ac-Di-Sol) | 3.00% | 3.00% | 3.00% |
| Disintegrant | Crospovidone (PVP-XL) | 3.00% | 3.00% | 3.00% |
| Glidant | Silicon dioxide (Syloid 244 FP) | 0.50% | 0.50% | 0.50% |
| Disintegration Aid | Sodium Chloride (NaCl Powder) | — | 5.00% | — |
| Disintegration Aid | 1:1 Sodium Chloride:Potassium Chloride | — | — | 5.00% |
| Lubricant | Magnesium Stearate | 0.25% | 0.25% | 0.25% |

TABLE 14

Exemplary spray-dried dispersion tablets.

| Function | Exemplary Ingredients | % w/w of Tablet |
|---|---|---|
| | Pregranulation | |
| Active (SDD) | 15/85 Compound A-HCl/HPMCAS-M, 15/85 Compound A-HCl/PVPVA 64, or 35/65 Compound A-HCl/PVPVA 64 | 20 to 35% |
| Filler(s) | Microcrystalline Cellulose, Mannitol | 20 to 60% |
| Disintegrant(s) | Pregelatinized Starch, Croscarmellose Sodium, Crospovidone | 5 to 30% |
| Disintegration Aid(s) | Sodium Chloride (NaCl Powder), 1:1 Sodium Chloride:Potassium Chloride | 0 to 10% |
| Glidant | Silicon dioxide | 0.25 to 1% |
| Lubricant | Magnesium Stearate | 0.25 to 1% |
| | Total Pregranulation | 70% to 85% |
| | Extragranular | |
| Filler(s) | Microcrystalline Cellulose | 0 to 20% |
| Disintegrant(s) | Croscarmellose Sodium, Crospovidone | 3 to 10% |
| Disintegration Aid(s) | Sodium Chloride (NaCl Powder), 1:1 Sodium Chloride:Potassium Chloride | 0 to 5% |
| Glidant | Silicon dioxide | 0.25 to 1% |
| Lubricant | Magnesium Stearate | 0.25 to 1% |
| | Total Extragranular | 15 to 30% |

A representative non-limiting description of the manufacturing process for the SDD tablets is as follows:

Stage 1: Spray Drying: Compound A-HCl and copovidone are dissolved in MeOH. The solution spray-dried. Spray-dried dispersion (Compound A-HCl SDD) is collected.

Stage 2: Roller Compaction: Granulation blend consisting of Compound A-HCl SDD, filler(s), disintegrant(s), glidant(s), and lubricant(s) are blended. In some embodiments, granulation blend consisting of Compound A-HCl SDD, mannitol, microcrystalline cellulose, crospovidone, colloidal silicon dioxide are prepared and blended. The intra-granular portion of the magnesium stearate is screened and added to the granulation blend. The resulting blend is blended. Granulation blend is charged into hopper of the roller compaction and compacted into ribbons. The ribbons are passed through mesh screen using in-line oscillating mill to break up the ribbons and mill into granules.

In some embodiments, the granulation blend comprises about 20% to about 35% (w/w of the final tablet weight) Compound A-HCl SDD. In some embodiments, the granulation blend comprises about 21%, about 22%, about 28%, 29%, about 33%, about 34% (w/w of the final tablet weight) Compound A-HCl SDD. In some embodiments, the Compound A-HCl SDD comprises a 15/85 Compound A-HCl/HPMCAS-M, 15/85 Compound A-HCl/PVPVA64, or 35/65 Compound A-HCl/PVPVA 64 SDD.

Stage 3: Blending: The intra-granular material is mixed with the extragranular excipients. Extragranular excipients comprise one or more excipients selected from: fillers, disintegrants, glidants, and lubricants. The extragranular components include microcrystalline cellulose, crospovidone, colloidal silicon dioxide. The extragranular lubricant, magnesium stearate, is sieved using an appropriately sized screen, then added to the blend and mixed.

Stage 4: Compression: The final blend is compressed into tablets.

Stage 5: Pan-Coating: Film coating suspension of Opadry White 03K18416. is prepared in purified water, and tablets are coated with Opadry White 03K18416 in a perforated coating pan.

Example 4

Evaluation of Formulation Performance in Dogs

Study Designs

Evaluated two conditions* in the dog: +Pg pretreatment (mimics human fasted stomach, pH 1-2) and −Pg pretreatment (mimics humans taking PPIs or antacids, pH 3-5). (*: 1-week washout between each condition; Pg=pentagastrin)

Compound A-HCl Solution

N=4 non-naïve dog. Vehicle: propylene glycol. Conditions: −Pg.

Compound A-HCl HMG capsule

N=4 non-naïve dog. Conditions: +Pg, −Pg.

Compound A-HCl Spray-Dried Dispersion Tablets: PVPVA 2 groups of N=6 non-naïve male dogs. Conditions: +Pg, −Pg.

Results from this study is presented in Tables 15 and 16.

TABLE 15

Dog PK evaluation of formulations of Compound A-HCl

| | | 20 mg HMG capsule | | 20 mg PVPVA SDD tablets | |
|---|---|---|---|---|---|
| PK Parameters | Solution (−Pg) | Fasted +Pg | Fasted −Pg | Fasted +Pg | Fasted −Pg |
| $C_{max}$ (ng/mL) | 191 ± 55.2 | 126 ± 99.6 | 14.2 ± 2.9 | 67.5 ± 41.3 | 125 ± 72.6 |
| $AUC_{0-t}$ (ng*hr/mL) | 1390 ± 559 | 874 ± 623 | 85.2 ± 32.6 | 366 ± 243 | 454 ± 226 |

TABLE 16

Dog PK evaluation of 60 mg 35/65 PVP-VA SDD tablet of Compound A-HCl

| PK | 35% SDD | 60 mg PVPVA SDD tablet | | |
|---|---|---|---|---|
| Parameters | Suspension | Tablet C3 | Tablet C4 | Tablet C5 |
| $C_{max}$ (ng/mL) | 437 ± 140 | 377 ± 129 | 329 ± 144 | 357 ± 146 |
| $AUC_{0-t}$ (ng*hr/mL) | 3630 ± 1990 | 3110 ± 1360 | 2540 ± 1120 | 2560 ± 1140 |

Figure 2:
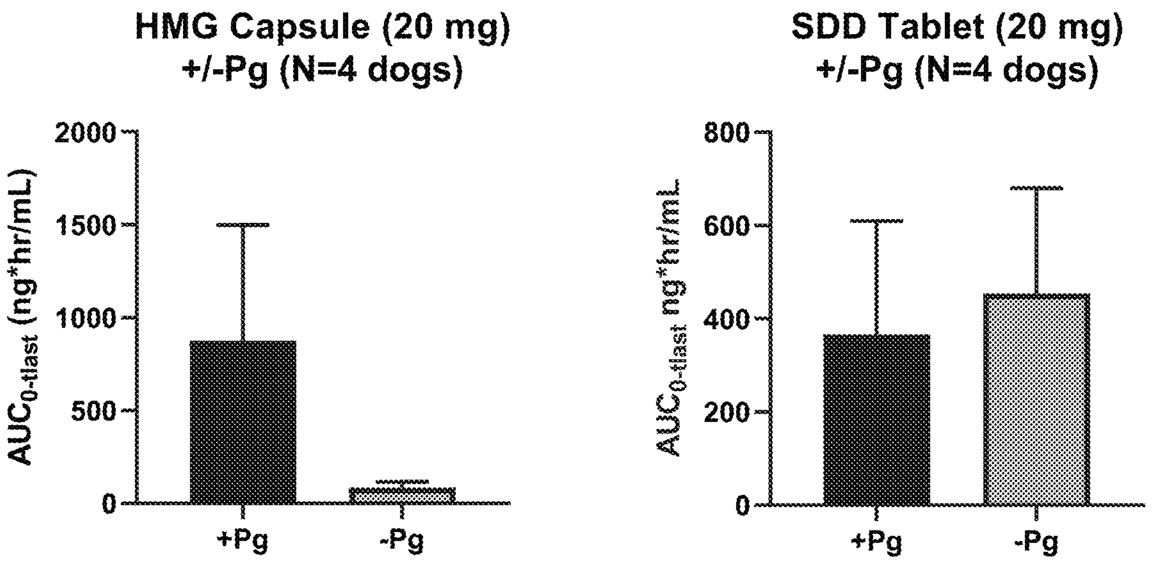
FIG. 2. Illustrates the performance of the HMG capsule formulation and the SDD tablet formulation of Compound A-HCl in dogs with or without pentagastrin pretreatment.

As shown in Table 15 and FIG. 2, the HMG capsule formulations performed poorly in dogs not pretreated with pentagastrin, whereas the spray-dried dispersions tablets performed better; For HMG capsule formulation, AUC without pentagastrin was only 11% of the AUC with pentagastrin (98.2 ng*hr/mL compared to 917 ng*hr/mL). In comparison, the AUC for the PVPVA SDD tablet formulations without pentagastrin was 185% and 124% of with pentagastrin condition, respectively. These data show that PVPVA SDD tablet formulations are superior under high gastric pH environment (e.g., as would be in subjects that are are taking PPI or antacids).

Example 5

A Phase 1, Multi-Cohort, Single Dose Study to Assess the Relative Bioavailability, Performance, and Safety of Two Formulations of Compound A The study was conducted in up to 3 cohorts, each with a specific primary objective:

Cohort 1: To characterize performance of 10 mg tablets prepared by spray-dried dispersion (SDD) of Compound A-HCl salt.

Cohort 2: To evaluate the relative bioavailability of 10 mg SDD tablets compared to the Compound A-HCl hot melt granulation (HMG) formulation, 10 mg capsules. To determine the effect of timing of food administration on pharmacokinetics of low dose of the 10 mg SDD tablets.

Cohort 3: To determine the effect of timing of food administration on pharmacokinetics of SDD tablets and dose proportionality in doses higher than 20 mg. To determine the optimal dosing regimen that results in adequate systemic exposure with short post-dose fasting duration.

Study Design:

Up to thirty-six (36) healthy male and female subjects were enrolled. Cohorts 1-2 consisted of four periods each, and Cohort 3 consisted of three periods.

Cohort 1:

The SDD tablets were evaluated. Up to twelve (12) healthy male and female subjects were enrolled in each cohort. Cohort 1 consisted of 4 periods: In Period 1, subjects were administered a proton-pump inhibitor (lansoprazole, 15 mg BID for 3 days (from Day −3), taken orally at least 30 min prior to a meal, once in the morning and once in the evening). On the fourth day (Day 1 of study), fasted subjects will take the last dose of lansoprazole (15 mg) 60 min prior to 20 mg Compound A (2×10 mg of the SDD tablets). In Period 2, fasted subjects were administered 20 mg Compound A (2×10 mg of the SDD tablets). In Period 3, fasted subjects were administered 20 mg Compound A (2×10 mg of the SDD tablets) with a high-fat, high-calorie meal. In Period 4, fasted subjects will take up to 80 mg Compound A (up to 8×10 mg of the SDD tablets). The actual dose was selected based on the pharmacokinetic data from Period 2.

For Period 1: In the evening before dosing (Day −1), subjects were administered their evening dose of 15 mg lansoprazole, provided an evening meal at least 30 min after administration of lansoprazole, and then were required to fast overnight (≥10 hr) on Day −1. On Day 1, they were administered the morning dose (last dose) of 15 mg lansoprazole at least 60 min prior to administration of Compound A (2×10 mg SDD tablets). Subjects continued to fast for 2 hr after Compound A, after which they were allowed to ingest a standard meal.

For Period 2: Subjects were required to fast overnight (≥10 hr) on Day 7. On Day 8, 20 mg Compound A (2×10 mg SDD tablets) was administered orally. Subjects continued to fast for 2 hr after Compound A, after which they were allowed to ingest a standard meal.

For Period 3: Subjects were required to fast overnight (≥10 hr) on Day 14. On Day 15, they were allowed to ingest a high-fat, high-calorie meal within 30 min. Upon completion of the ingestion of the meal, Compound A (2×10 mg SDD tablets) was administered (no more than 30 min after the start of the meal). No additional food was provided for at least 4 hr after administration of Compound A.

Subjects were not allowed to perform strenuous exercise of >30 min/day 3 days prior to Day −1 and throughout the study.

PK and safety assessments including adverse event (AE) monitoring, clinical laboratory tests, vital sign measurements, 12-lead ECGs, Holter and telemetry monitoring (Period 4 only), and physical examinations were conducted at scheduled times throughout the study.

Cohort 2:

The cohort consisted of four periods. In each period, a single dose of 20 mg Compound A (2×10 mg SDD) was administered orally.

For Period 1: Subjects were required to fast overnight (≥10 hr) on Day −1. On Day 1, a low-fat meal was given 2 hours after administration of 20 mg Compound A (2×10 mg HMG capsules; reference formulation).

For Period 2: Subjects were required to fast overnight (≥10 hr) on Day 7. On Day 8, they were given a low-fat meal 2 hr after administration of 20 mg Compound A (2×10 mg SDD tablets; test formulation).

For Period 3: Subjects were required to fast overnight (≥10 hr) on Day 14. On Day 15, they were given a low-fat meal 1 hr after administration of 20 mg Compound A (2×10 mg SDD tablets).

For Period 4: Subjects were required to fast overnight (≥10 hr) on Day 21. On Day 22, they were given a low-fat meal 0.5 hr after administration of 20 mg Compound A (2×10 mg SDD tablets).

The final study visit occured on Day 29. Subjects were not allowed to perform strenuous exercise of >30 min/day, 3 days prior to Day −1 and throughout the study. PK and safety assessments including adverse event (AE) monitoring, clinical laboratory tests, vital sign measurements, 12-lead ECGs, and physical examinations were conducted at scheduled times throughout the study.

Cohort 3:

The cohort consisted of three periods. In each period, a single dose of Compound A SDD (40, 60, or 80 mg) was administered orally (4×10 mg SDD tablets, 6×10 mg SDD tablets, or 8×10 mg SDD tablets). There was a washout period of at least 10 days between each dose of Compound A.

For Period 1: Subjects were required to fast overnight (≥10 hr) on Day −1. On Day 1, they were given a standard meal 1 hr after administration of 40 mg Compound A (4×10 mg SDD tablets).

For Period 2: Subjects were required to fast overnight (≥10 hr) on Day 10. On Day 11, they were given a standard meal 1 hr or 2 hr after administration of 80 Compound A (8×10 mg SDD tablets). The timing of the meal (1 hr or 2 hr post administration of Compound A) was dependent on the mean $AUC_{0-24}$ determined in Period 1.

For Period 3: Subjects were required to fast overnight (≥10 hr) on Day 20. On Day 21, they were given a standard meal 1 hr or 4 hr after administration of 60 or 80 mg Compound A (6×10 mg SDD tablets or 8×10 mg SDD tablets). The dose and timing of the standard meal was dependent on the mean $AUC_{0-24}$ determined in Period 2.

The final study visit occured on Day 29. Subjects were not allowed to perform strenuous exercise of >30 min/day, 3 days prior to Day −1 and throughout the study. PK and safety assessments including adverse event (AE) monitoring, clinical laboratory tests, vital sign measurements, 12-lead ECGs, and physical examinations were conducted at scheduled times throughout the study.

Study Population:

Up to 36 healthy male or female subjects, between the ages of 18 to 55 years, inclusive, were enrolled. For Cohort 2 only, male and female subjects 18 to 65 years of age, inclusive, at the time of screening.

Inclusion Criteria

Each subject had to meet all of the following inclusion criteria to be enrolled in the study: Male and female subjects 18 to 55 years of age, inclusive, at the time of screening. For cohort 2 only, male and female subjects 18 to 65 years of age, inclusive, at the time of screening. Body mass index (BMI) of 18 to 30 kg/m$^2$, inclusive. Willing to refrain from strenuous, unaccustomed exercise and sports, defined as greater than 30 minutes per day, 3 days prior to Day −1 and throughout the study. If the subject was a heterosexual or bisexual female, she had to be of non-childbearing potential OR must agree to use a highly effective or two clinically acceptable methods of contraception.

Exclusion Criteria

A healthy subject meeting any of the following criteria was to be excluded from the study: Prior treatment with Compound A. Any uncontrolled or active major systemic disease which makes study participation unsafe or could interfere with evaluation of the endpoints of the study. History or presence of malignancy except adequately treated basal cell or squamous cell carcinomas of the skin within the past 5 years. Active acute or chronic infection. Use of any investigational drug within the past 60 days or 5 half-lives, whichever is longer, prior to the first dosing of study drug. Use of tobacco and/or nicotine-containing products, recreational drugs, or alcohol for 48 hr prior to admission and agreement to refrain from use throughout the study. History of or current alcohol abuse and/or other drug addiction <1 year prior to screening. Used any prescription or over-the-counter (OTC) medication or alternative medicinal products within 14 days of Day −1. Use of caffeine-containing beverages or food for 48 hr prior to Day −1 and for 48 hr prior to each check-in day for all subsequent periods. Have ingested foods containing poppy seeds within 7 days before screening until completion of the study assessments. Taking moderate or strong CYP3A4 inhibitors or inducers. Strenuous exercise for >30 min/day, 3 days prior to Day −1 and throughout the study. Had a blood loss ≥500 mL or donated blood within 3 months prior to admission. Have amylase and/or lipase levels >2×ULN, alanine aminotransferase (ALT) and/or aspartate aminotransferase (AST) >2×ULN, total bilirubin >1.5×ULN (except in the case of known Gilbert's syndrome), and/or serum creatinine above the upper limit of normal. History of hypersensitivity reactions to any excipients in the study drug. Tested positive at screening for human immunodeficiency virus (HIV), hepatitis B surface antigen (HBsAg), or hepatitis C antibody (HCV-Ab), or has a history of a positive result. Female subjects who have a positive serum pregnancy test or are breastfeeding. For Cohort 1 only, subjects that are classified as CYP2C19 poor metabolizers or ultra-rapid metabolizers.

Test Product, Dose, and Mode of Administration:

10 mg tablets (SDD). Multiple tablets were swallowed with water depending on dose specified for a given period/cohort.

Reference Therapy, Dose, and Mode of Administration:

10 mg HMG capsule formulation served as the reference formulation. Multiple capsules were swallowed with water depending on dose specified for a given period/cohort.

Plasma Pharmacokinetic Parameters:

Blood PK samples were collected to evaluate Compound A plasma concentrations.

PK parameters were calculated for Compound A and the following are shown in tables below: Area under the plasma concentration curve from 0 to 24 hours ($AUC_{0-24}$); Maximum plasma concentration ($C_{max}$); Time to achieve maximum plasma concentration ($T_{max}$);

Results

Results from this clinical trial showed that the co-administration of proton pump inhibitors only had a small effect on the pharmacokinetics observed with the administration of the SDD tablets, shorter fasting times are realized with the SDD tablets and the SDD tablets provide better dose proportional pharmacokinetics.

Results from Cohort 1 is presented in Table 17.

TABLE 17

| Results from Cohort 1 | Mean | SD | CV % |
|---|---|---|---|
| Period 1 (SDD 20 mg + PPI) | | | |
| $T_{max}$ (hr) | | 2 (1.5-3) | |
| $C_{max}$ (ng/mL) | 92.5 | 21.6 | 23.3 |
| $AUC_{0-24}$ (hr*ng/mL) | 891 | 240 | 26.9 |
| Period 2 (SDD 20 mg alone) | | | |
| $T_{max}$ (hr) | | 3 (1.5-6) | |
| $C_{max}$ (ng/mL) | 114 | 40.6 | 35.5 |
| $AUC_{0-24}$ (hr*ng/mL) | 1140 | 337 | 29.5 |

TABLE 17-continued

| Results from Cohort 1 | Mean | SD | CV % |
|---|---|---|---|
| Period 3 (SDD 20 mg + food) | | | |
| $T_{max}$ (hr) | | 1.8 (1.3-4) | |
| $C_{max}$ (ng/mL) | 16.7 | 6.82 | 40.9 |
| $AUC_{0-24}$ (hr*ng/mL) | 155 | 46.3 | 29.9 |
| Period 4 (SDD 60 mg) | | | |
| $T_{max}$ (hr) | | 3 (1-6) | |
| $C_{max}$ (ng/mL) | 305 | 139 | 45.4 |
| $AUC_{0-24}$ (hr*ng/mL) | 2900 | 1240 | 42.6 |
| P4/P2 Ratio | | | |
| $C_{max}$ | | 3.0 (1.7-3.4) | |
| $AUC_{0-24}$ | | 2.8 (1.6-3.7) | |

Median and range are reported for $T_{max}$. Mean and range are reported for P4/P2 ratios. All dose administered with overnight fast and 2 h post dose fast. Food: high fat meal.

Cohort 1 (SDD 10 mg×2 under different conditions): the observed exposures with and without PPI are fairly comparable. Cohort 1 (SDD 10 mg×2 vs. 10 mg×6): Relatively dose proportional increases in exposures were observed.

In comparison to the SDD tablets, relatively dose proportional increases in exposures were not observed with the HMG capsules. See FIG. 1. Dose proportionality data for the HMG capsules obtained from a previous clinical study is presented in Table 18.

TABLE 18

Comparative data: Dose Proportionality Observed for HMG Capsule Formulations after single dose (4 h post dose fast).

| Parameter (Mean) | Day | 5 mg (n = 5) | 10 mg (n = 6) | 20 mg (n = 5) | 30 mg (n = 5) | 40 mg (n = 6) | 60 mg (n = 6) |
|---|---|---|---|---|---|---|---|
| Tmax (hr) | 1 | 1.2 ± 0.11 | 1.8 ± 0.94 | 2.4 ± 0.82 | 1.4 ± 0.91 | 3.4 ± 1.1 | 3.0 ± 1.2 |
| $C_{max}$ (ng/mL) | 1 | 16.8 ± 7.22 | 78.7 ± 45.3 | 88.7 ± 43.3 | 78.2 ± 60.7 | 185 ± 118 | 154 ± 77.6 |
| $AUC_{0-24}$ (ng hr/mL) | 1 | 167 ± 73.4 | 661 ± 340 | 811 ± 409 | 578 ± 411 | 1770 ± 888 | 1450 ± 656 |

Data shown are mean ± standard deviation

Results from Cohort 2 is presented in Table 19.

TABLE 19

| Results from Cohort 2 | Mean | SD | CV % |
|---|---|---|---|
| Period 1 (HMG 2 h fast) | | | |
| $T_{max}$ (hr) | | 2 (0.75-3) | |
| $C_{max}$ (ng/mL) | 123 | 54.4 | 44.4 |
| $AUC_{0-24}$ (hr*ng/mL) | 1060 | 462 | 43.6 |
| Period 2 (SDD 2 h fast) | | | |
| $T_{max}$ (hr) | | 2 (1-3) | |
| $C_{max}$ (ng/mL) | 97.2 | 32.8 | 33.7 |
| $AUC_{0-24}$ (hr*ng/mL) | 877 | 320 | 36.5 |
| Period 3 (SDD 1 h fast) | | | |
| $T_{max}$ (hr) | | 1.4 (0.75-4) | |
| $C_{max}$ (ng/mL) | 89.3 | 37.0 | 41.4 |
| $AUC_{0-24}$ (hr*ng/mL) | 721 | 319 | 44.2 |
| Period 4 (SDD 30 min fast) | | | |
| $T_{max}$ (hr) | | 1.3 (0.75-4) | |
| $C_{max}$ (ng/mL) | 81.3 | 26.8 | 32.9 |
| $AUC_{0-24}$ (hr*ng/mL) | 630 | 212 | 33.6 |

TABLE 19-continued

| Results from Cohort 2 | | | |
|---|---|---|---|
| | Mean | SD | CV % |
| P3/P2 Ratio (%) | | | |
| $C_{max}$ | | 92% | |
| $AUC_{0-24}$ | | 82% | |

All dose administered with overnight fast.

Cohort 2 (SDD 10 mg×2 vs. HMG and under different post-dose fasting durations): SDD tablets did not appear to have better exposures than HMG capsules and the two formulations were relatively comparable. For the SDD tablets the $AUC_{0-24}$ (a measure of extent of absorption) after a 1 hr post dose fast was decreased to 82% of that obsereved with 2 hr post-dose fast, which is a relatively small decrease in exposure.

In comparison to the performance of the SDD tablets under different post-dose fasting duration scenarios, the HMG capsules performed poorly under different post-dose fasting duration scenarios in a previously completed clinical study. Pharmacokinetic data obtained after administering a 20 mg dose (10 mg HMG capsule×2) in 12 subjects (N=4 male, N=8 Female) is presented in Table 20.

TABLE 20

Comparative Data: HMG capsule Performance Under Different Post-Dose Fasting Durations

| Post-Dose Fasting Duration | $T_{max}$ (Hr) | $C_{max}$ (ng/mL) | $AUC_{0-24}$ (Hr*ng/mL) |
|---|---|---|---|
| 4 hour | 0.75-6 | 134 (48.9) | 1280 (344) |
| 2 hour | 0.75-3 | 104 (35.5) | 930 (293) |
| 1 hour | 0.75-3 | 92.2 (30.6) | 654 (244) |
| Ratio (%): 2 hr/1 hr | — | 89% | 70% |

Cmax and $AUC_{0-24}$ data show are mean (standard deviation). Range is shown for Tmax.

With the HMG capsule formulations, approximatley 30% loss in extent of absorption was noted with a 1-hour post-dose fasting vs. a 2-hour post-dose fast.

HMG capsules with a 2 h fast was evaluated in Phase 2 clinical studies. A 1 hour fast is more desirable than a 2 hour fast. Only 18% loss of $AUC_{(0-24)}$ was observed with 1 hour fast compared to a 2 hour fast. SDD 1 h fast will be utilized for Phase 3. Importantly, SDD tablets appeared to have better dose proportionality than HMG capsules, allowing for 3.0× dose (i.e., 60 mg) to be administered in Phase 3 clinical studies.

The examples and embodiments described herein are for illustrative purposes only and various modifications or changes suggested to persons skilled in the art are to be included within the spirit and purview of this application and scope of the appended claims.

What is claimed is:

1. A spray-dried solid dispersion comprising:

(a) 3-[4-(4-amino-piperidin-1-yl)-3-(3,5-difluoro-phenyl)-quinolin-6-yl]-2-hydroxy-benzonitrile monohydrochloride; and (b) a pharmaceutically acceptable polymer selected from hydroxypropyl methylcellulose acetate succinate (HPMCAS) and polyvinylpyrrolidone polyvinyl acetate copolymers (PVP/VA);

wherein the 3-[4-(4-amino-piperidin-1-yl)-3-(3,5-difluoro-phenyl)-quinolin-6-yl]-2-hydroxy-benzonitrile monohydrochloride is dispersed in a polymer matrix formed from the pharmaceutically acceptable polymer.

2. The spray-dried solid dispersion of claim 1, wherein the pharmaceutically acceptable polymer is HPMCAS.

3. The spray-dried solid dispersion of claim 2, wherein the HPMCAS is has an acetyl content of 7-11%.

4. The spray-dried solid dispersion of claim 1, wherein the pharmaceutically acceptable polymer is PVP/VA.

5. The spray-dried solid dispersion of claim 4, wherein the PVP/VA has a weight ratio of polyvinylpyrrolidone to vinyl acetate of about 6:4.

6. The spray-dried solid dispersion of claim 1 wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:1 to about 1:10.

7. The spray-dried solid dispersion of claim 6, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:4 to about 1:7.

8. The spray-dried solid dispersion of claim 6, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:5 to about 1:6.

9. The spray-dried solid dispersion of claim 6, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:1 to about 1:2.

10. The spray-dried solid dispersion of claim 1 wherein the spray-dried solid dispersion comprises at least 10% by weight of the 3-[4-(4-amino-piperidin-1-yl)-3-(3,5-difluoro-phenyl)-quinolin-6-yl]-2-hydroxy-benzonitrile monohydrochloride; wherein the % by weight of the 3-[4-(4-amino-piperidin-1-yl)-3-(3,5-difluoro-phenyl)-quinolin-6-yl]-2-hydroxy-benzonitrile monohydrochloride is calculated using the weight equivalent amount of 3-[4-(4-amino-piperidin-1-yl)-3-(3,5-difluoro-phenyl)-quinolin-6-yl]-2-hydroxy-benzonitrile in the spray-dried solid dispersion.

11. The spray-dried solid dispersion of claim 10, wherein the spray-dried solid dispersion comprises about 15% by weight of the 3-[4-(4-amino-piperidin-1-yl)-3-(3,5-difluoro-phenyl)-quinolin-6-yl]-2-hydroxy-benzonitrile monohydrochloride.

12. The spray-dried solid dispersion of claim 1 wherein the spray-dried solid dispersion comprises at least 25% by weight of the 3-[4-(4-amino-piperidin-1-yl)-3-(3,5-difluoro-phenyl)-quinolin-6-yl]-2-hydroxy-benzonitrile monohydrochloride; wherein the % by weight of the 3-[4-(4-amino-piperidin-1-yl)-3-(3,5-difluoro-phenyl)-quinolin-6-yl]-2-hydroxy-benzonitrile monohydrochloride is calculated using the weight equivalent amount of 3-[4-(4-amino-piperidin-1-yl)-3-(3,5-difluoro-phenyl)-quinolin-6-yl]-2-hydroxy-benzonitrile in the spray-dried solid dispersion.

13. The spray-dried solid dispersion of claim 12, wherein the spray-dried solid dispersion comprises about 35% by weight of the 3-[4-(4-amino-piperidin-1-yl)-3-(3,5-difluoro-phenyl)-quinolin-6-yl]-2-hydroxy-benzonitrile monohydrochloride.

14. The spray-dried solid dispersion of claim 5, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:1 to about 1:10.

15. The spray-dried solid dispersion of claim 14, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:4 to about 1:7.

16. The spray-dried solid dispersion of claim 14, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:5 to about 1:6.

17. The spray-dried solid dispersion of claim 14, wherein the weight ratio of the 3-[4-(4-amino-piperidin-1-yl)-3-(3,5-difluoro-phenyl)-quinolin-6-yl]-2-hydroxy-benzonitrile monohydrochloride to the pharmaceutically acceptable polymer is from about 1:1 to about 1:2.

18. The spray-dried solid dispersion of claim 5, wherein the spray-dried solid dispersion comprises at least 10% by weight of the 3-[4-(4-amino-piperidin-]-yl)-3-(3,5-difluoro-phenyl)-quinolin-6-yl]-2-hydroxy-benzonitrile monohydrochloride; wherein the % by weight of the 3-[4-(4-amino-piperidin-1-yl)-3-(3,5-difluoro-phenyl)-quinolin-6-yl]-2-hydroxy-benzonitrile monohydrochloride is calculated using the weight equivalent amount of 3-[4-(4-amino-piperidin-1-yl)-3-(3,5-difluoro-phenyl)-quinolin-6-yl]-2-hydroxy-benzonitrile in the spray-dried solid dispersion.

19. The spray-dried solid dispersion of claim 18, wherein the spray-dried solid dispersion comprises about 15% by weight of the 3-[4-(4-amino-piperidin-1-yl)-3-(3,5-difluoro-phenyl)-quinolin-6-yl]-2-hydroxy-benzonitrile monohydrochloride.

20. The spray-dried solid dispersion of claim 5, wherein the spray-dried solid dispersion comprises at least 25% by weight of the 3-[4-(4-amino-piperidin-1-yl)-3-(3,5-difluoro-phenyl)-quinolin-6-yl]-2-hydroxy-benzonitrile monohydrochloride; wherein the % by weight of the 3-[4-(4-amino-piperidin-1-yl)-3-(3,5-difluoro-phenyl)-quinolin-6-yl]-2-hydroxy-benzonitrile monohydrochloride is calculated using the weight equivalent amount of 3-[4-(4-amino-piperidin-1-yl)-3-(3,5-difluoro-phenyl)-quinolin-6-yl]-2-hydroxy-benzonitrile in the spray-dried solid dispersion.

21. The spray-dried solid dispersion of claim 20, wherein the spray-dried solid dispersion comprises about 35% by weight of the 3-[4-(4-amino-piperidin-1-yl)-3-(3,5-difluoro-phenyl)-quinolin-6-yl]-2-hydroxy-benzonitrile monohydrochloride.

* * * * *